US012134773B1

United States Patent
Guo et al.

(10) Patent No.: US 12,134,773 B1
(45) Date of Patent: Nov. 5, 2024

(54) MYCOVIRUS-INDUCED GENE SILENCING VECTOR, CONSTRUCTION METHOD AND APPLICATION THEREOF

(71) Applicants: Institute of Plant Protection(IPP), Chinese Academy of Agricultural Sciences(CAAS), Beijing (CN); Beijing Zhongbao Green Agricultural Science and Technology Group Co., Ltd, Beijing (CN)

(72) Inventors: Lihua Guo, Beijing (CN); Chang Chen, Beijing (CN); Lihang Zhang, Beijing (CN); Shuangchao Wang, Beijing (CN); Shaojian Ruan, Beijing (CN); Jun Xu, Beijing (CN); Yijun Zhao, Beijing (CN)

(73) Assignees: INSTITUTE OF PLANT PROTECTION(IPP), CHINESE ACADEMY OF AGRICULTURAL SCIENCES (CAAS), Beijing (CN); BEIJING ZHONGBAO GREEN AGRICULTURAL SCIENCE AND TECHNOLOGY GROUP CO., LTD, Beijing (CN)

( * ) Notice: Subject to any disclaimer, the term of this patent is extended or adjusted under 35 U.S.C. 154(b) by 0 days.

(21) Appl. No.: 18/529,537

(22) Filed: Dec. 5, 2023

Related U.S. Application Data

(63) Continuation of application No. PCT/CN2023/097344, filed on May 31, 2023.

Foreign Application Priority Data

Apr. 23, 2023 (CN) .......................... 202310441503.1

(51) Int. Cl.
| | | |
|---|---|---|
| C12N 15/09 | (2006.01) | |
| C12N 9/10 | (2006.01) | |
| C12N 9/16 | (2006.01) | |
| C12N 15/10 | (2006.01) | |
| C12N 15/113 | (2010.01) | |
| C12N 15/80 | (2006.01) | |
| C12R 1/77 | (2006.01) | |

(52) U.S. Cl.
CPC .......... *C12N 15/80* (2013.01); *C12N 9/1029* (2013.01); *C12N 9/16* (2013.01); *C12N 15/102* (2013.01); *C12N 2750/00022* (2013.01); *C12N 2750/00031* (2013.01); *C12N 2750/00043* (2013.01); *C12R 2001/77* (2021.05)

(58) Field of Classification Search
None
See application file for complete search history.

(56) References Cited

FOREIGN PATENT DOCUMENTS

| CN | 109666655 | * | 4/2019 |
|---|---|---|---|
| CN | 109666655 A | | 4/2019 |
| CN | 109810997 | * | 5/2019 |
| CN | 109810997 A | | 5/2019 |
| CN | 110922457 A | | 3/2020 |
| CN | 113136391 A | | 7/2021 |
| CN | 114317598 A | | 4/2022 |

OTHER PUBLICATIONS

GenBank MK430077.1 (printed May 29, 2024).*
GenBank MK430077.2 (printed May 29, 2024).*
Li et al (Science Advances, 2020, eaay9634, 9 pages).*
CN109666655 English translation (2019).*
CN109810997 English translation (2019).*
Li et al Supplemental Material (Science Advances, 2020, eaay9634).*
Pengfei Li et al., "A tripartite ssDNA mycovirus from a plant pathogenic fungus is infectious as cloned DNA and purified virions," Science Advances, Apr. 2020, vol. 6.
Lihang Zhang et al., "Molecular Characterization of a Novel Strain of Fusarium graminearum Virus 1 Infecting Fusarium graminearum," Viruses, Mar. 2020, 12, 357.
Jisuk Yu et al., "Molecular Characterization of Fusarium Graminearum Virus 2 Isolated from Fusarium graminearum Strain 98-8-60," Plant Pathol. J., Jun. 2011, pp. 285-290, vol. 27, No. 3.
Li Ke et al., "Prokaryotic expression of FpgMBV1-P3 and preparation of its polyclonal antibodies," Acta Phytopathologica Sinica, Jan. 2020, pp. 567-573, vol. 50, No. 5. (abstract translated).
Polina Tretiakova et al., "Successful Silencing of the Mycotoxin Synthesis GeneTRI5inFusarium culmorumand Observation of Reduced Virulence inVIGS and SIGS Experiments," Genes, Feb. 2022, 13, 395.
Search Report for China Application No. 202310441503.1, dated Aug. 21, 2023.
Notification to Grant Patent for China Application No. 202310441503.1, dated Aug. 23, 2023.
International Search Report for PCT/2023/097344, mailed Nov. 13, 2023.

* cited by examiner

*Primary Examiner* — Laura B Goddard
(74) *Attorney, Agent, or Firm* — Pilloff Passino & Cosenza LLP; Rachel Pilloff; Sean Passino

(57) ABSTRACT

A mycovirus-induced gene silencing vector and a construction method and an application thereof are provided. A nucleotide sequence of the mycovirus-induced gene silencing vector is shown in SEQ ID NO: 2, and construction method for the mycovirus-induced gene silencing vector includes: (1) connecting three single-stranded circular DNA molecules DNA-A, DNA-B and DNA-C of the mycovirus FgGMTV1/HB58 in series and introducing them into a same vector to construct a recombinant vector; and (2) carrying out a deletion mutation on a coding protein p26 of the DNA-C molecule in the recombinant vector to obtain the mycovirus-induced gene silencing vector.

6 Claims, 25 Drawing Sheets

Specification includes a Sequence Listing.

FIG. 7D

MYCOVIRUS-INDUCED GENE SILENCING VECTOR, CONSTRUCTION METHOD AND APPLICATION THEREOF

CROSS-REFERENCE TO RELATED APPLICATIONS

This application is a continuation of PCT/CN2023/097344, filed on May 31, 2023, and claims priority of Chinese Patent Application No. 202310441503.1, filed on Apr. 23, 2023, the entire contents of which are incorporated herein by reference.

INCORPORATION BY REFERENCE STATEMENT

This statement, made under Rules 77 (b) (5) (ii) and any other applicable rule incorporates into the present specification of an XML file for a "Sequence Listing XML" (see Rule 831 (a)), submitted via the USPTO patent electronic filing system or on one or more read-only optical discs (see Rule 1.52 (e) (8)), identifying the names of each file, the date of creation of each file, and the size of each file in bytes as follows:
File name: sequence_347095_12676
Creation date: Nov. 2, 2023
Byte size: 50,704

TECHNICAL FIELD

The disclosure relates to the field of genetic engineering, and in particular to a mycovirus-induced gene silencing vector and a construction method and application thereof.

BACKGROUND

Virus-induced gene silencing (VIGS) is a technique to study the function of plant genes by RNA-mediated plant antiviral mechanism. The principle is to insert the target gene fragment into the virus vector and infect the host plant. While the immune system of the plant recognizes the virus and the target gene, it degrades the endogenous target gene mRNA, causing the plant to have a phenotype of loss of function or decreased expression level of the target gene. When VIGS is initiated, a large number of double-stranded RNA (dsRNA) are synthesized by RNA-mediated RNA polymerase. In cells, dsRNA is cleaved into 19-24nt silencing RNA (siRNA) by Dicer analogues of RNaseIII family-specific endonucleases. SiRNA binds to a specific protein in the form of a single strand to form an RNA-induced silencing complex (RISC). The RISC is capable of specifically binding to the mRNA of the target gene in cytoplasm, leading to the degradation of the mRNA of the target gene, so that the infected plant shows the mutation trait of the target gene, thus directly inferring the function of the target gene or providing indirect biological evidence. Under ongoing development and in depth research, the VIGS technology has been widely used in the research and identification of related functional genes such as plant resistance, growth and development, and metabolic regulation, and has a good development and application prospect in plant trait improvement and plant protection.

*Fusarium graminearum* gemytripvirus 1 (FgGMTV 1) is a multi-component single-stranded circular DNA virus, which contains three single-stranded circular DNA fragments: DNA-A, DNA-B and DNA-C, with molecular sizes of 1316nt, 1320nt and 1309nt respectively and encoded with replication initiation protein (REP), Coat protein, CP) and unknown functional protein respectively. An infectious clone of FgGMTV1 has been successfully constructed in Mycovirus lab in Institute of Plant Protection (IPP), Chinese Academy of Agricultural Sciences (CAAS), and the relationship among the components is made clear: DNA-A and DNA-B are necessary for virus replication and infection, and their co-infection is capable of significantly inhibiting the growth, conidial production and pathogenicity of host fungi, but the virus is unstable and does not spread vertically through conidia; the replication and proliferation of DNA-C depend on DNA-A and DNA-B. The virus containing three components is stable and is capable of spreading through conidia, but it does not affect the phenotype and pathogenicity of host fungi. Therefore, it is possible to construct the vector of VIGS by artificial transfection with the infectious clone of FgGMTV1 as the basic element.

Wheat *Fusarium* head blight (FHB) is a worldwide wheat disease mainly caused by *Fusarium graminearum* complex. How to prevent the FHB and its toxin pollution is particularly urgent and important, which is directly related to food safety, food security and people's health. Chemical control is still an important measure for FHB control at present, but excessive dependence on chemical control leads to the resistance of pathogenic fungi to fungicides. In addition, due to the lack of wheat varieties with high resistance to the FHB, wheat FHB remains happening frequently at present and even for a long time to come. It is particularly important to find and explore new control methods of wheat FHB. By successfully constructing the VIGS vector of FgGMTV1 and silencing the genes related to host pathogenicity and toxin production, the obtained hypovirulent strains may be used as biological control factors, providing a new method for controlling the wheat FHB. Meanwhile, the obtained VIGS vector is capable of being widely used to study the gene function of *Fusarium graminearum*, which solves the problem that a gene knockout method fails to study the lethal genes.

SUMMARY

The objective of the present disclosure is to provide a mycovirus-induced gene silencing vector and its construction method and disclosure, so as to solve the problems existing in the prior art. The gene silencing vector induced by *Fusarium graminearum* single-stranded circular DNA virus FgGMTV1 is capable of effectively reducing the toxin production and pathogenicity of infected *Fusarium graminearum*, and provide a new direction for preventing and controlling wheat *Fusarium* head blight (FHB).

In order to achieve the above objectives, the present disclosure provides the following scheme.

The disclosure provides a mycovirus-induced gene silencing vector, and a nucleotide sequence of the mycovirus-induced gene silencing vector is shown in SEQ ID NO: 2.

The disclosure also provides a construction method for the mycovirus-induced gene silencing vector, including following steps:
S1, connecting three single-stranded circular DNA molecules DNA-A, DNA-B and DNA-C of mycovirus FgGMTV1/HB58 in series and introducing into a same vector to construct a recombinant vector; and
S2, carrying out a deletion mutation on a coding protein p26 of the DNA-C molecule in the recombinant vector to obtain a mycovirus-induced gene silencing vector.

Optionally, 1.3 copies of the DNA-A, 1.3 copies of the DNA-B and 1.5 copies of the DNA-C are connected in series and then connected to pBluescript II SK(+) to construct the recombinant vector.

Optionally, a nucleotide sequence of the DNA-A is shown in SEQ ID NO: 5, a nucleotide sequence of the DNA-B is shown in SEQ ID NO: 6, and a nucleotide sequence of the DNA-C is shown in SEQ ID NO: 7.

Optionally, the deletion mutation is a deletion of a sequence of 454-603nt of the coding protein p26 of the DNA-C.

The disclosure also provides a recombinant *Fusarium graminearum* including the mycovirus-induced gene silencing vector.

Optionally, the mycovirus-induced gene silencing vector carries exogenous genes. The exogenous genes include Tri101 gene and FgPP1 gene.

The disclosure also provides an application of the mycovirus-induced gene silencing vector or the recombinant *Fusarium graminearum* in preventing and controlling wheat FHB.

The disclosure also provides an application of the mycovirus-induced gene silencing vector or the recombinant *Fusarium graminearum* in preparing a preparation for preventing and controlling wheat FHB.

The disclosure discloses the following technical effects.

On the basis of previous research, the disclosure shortens the repetitive sequences of components DNA-A, DNA-B and DNA-C, and connects the three components in series to the same vector, and then selects the candidate mutant p26-D4 suitable as a VIGS vector by performing serial deletion mutation on the coding protein p26 of the DNA-C component. Through experimental verification, the constructed VIGS silencing vector p26-D4 is capable of accommodating 75-150 bp of exogenous genes, and effectively silence target genes such as GPF, Tri101 and FgPP1 in the wild *Fusarium graminearum* strain PH-1, which further verifies that this silencing vector p26-D4 carries exogenous genes to infect the *Fusarium graminearum* strain and is capable of effectively controlling wheat FHB. Therefore, the silencing vector p26-D4 provided by the disclosure offers a new direction for the prevention and control of wheat FHB.

BRIEF DESCRIPTION OF THE DRAWINGS

Figure 7D:
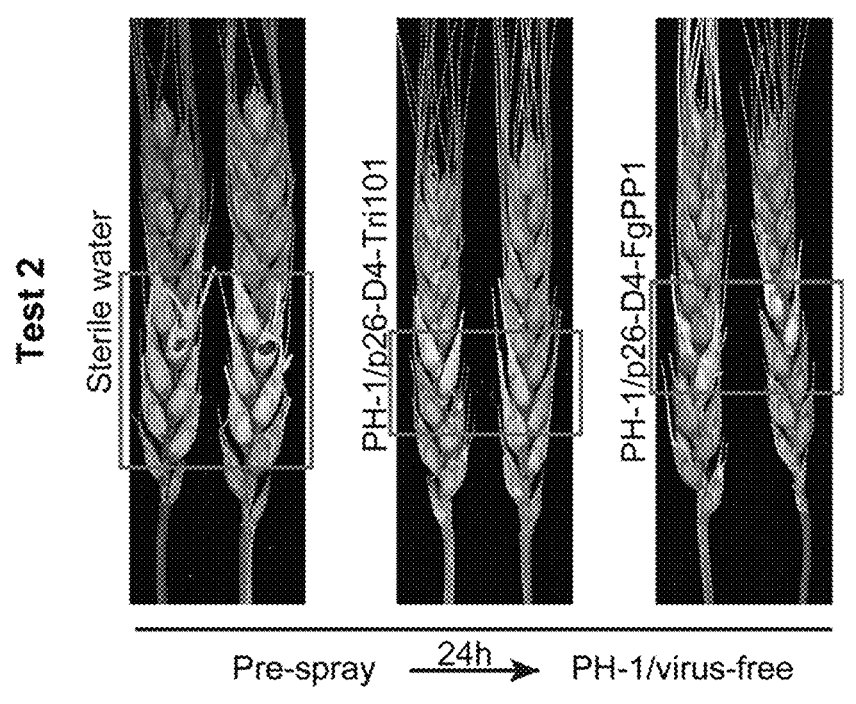

FIG. 7D shows wheat FHB symptom after control of hypovirulent strains infected by p26-D4-Tri101 and p26-D4-FgPP1 measured by pre-spray method (Test 2).

DETAILED DESCRIPTION OF THE EMBODIMENTS

A number of exemplary embodiments of the present disclosure are now described in detail, and this detailed description should not be considered as a limitation of the present disclosure, but should be understood as a more detailed description of certain aspects, characteristics and embodiments of the present disclosure.

The *Fusarium graminearum* single-stranded DNA virus FgGMTV1 used in the embodiments of the present disclosure is isolated and identified by Mycovirus lab in Institute of Plant Protection (IPP), Chinese Academy of Agricultural Sciences (CAAS), see Li P. (2020). A tripartite ssDNA mycovirus from a plant pathogenic fungus is infectious as cloned DNA and purified viruses. Science Advances 6, eaay9634. The wild *Fusarium graminearum* strain PH-1 and the *Fusarium graminearum* strain PH-1/GFP with green fluorescent label are preserved in the Mycovirus lab in IPP, CAAS.

Figure 1:
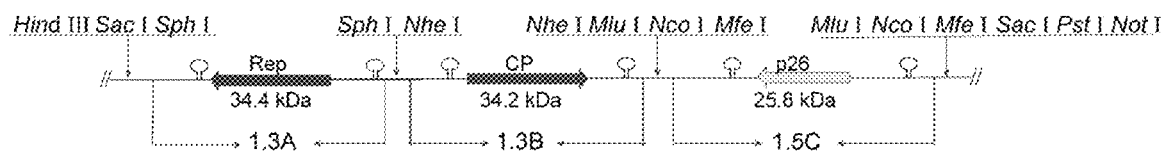
FIG. 1 is a schematic structural diagram of an infectious clone pSK-ABC.
Figure 2A:
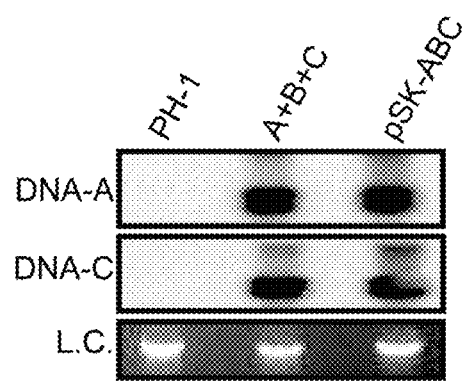
FIG. 2A shows Southern blot detection (results) of a pSK-ABC transfectant.
Figure 2B:
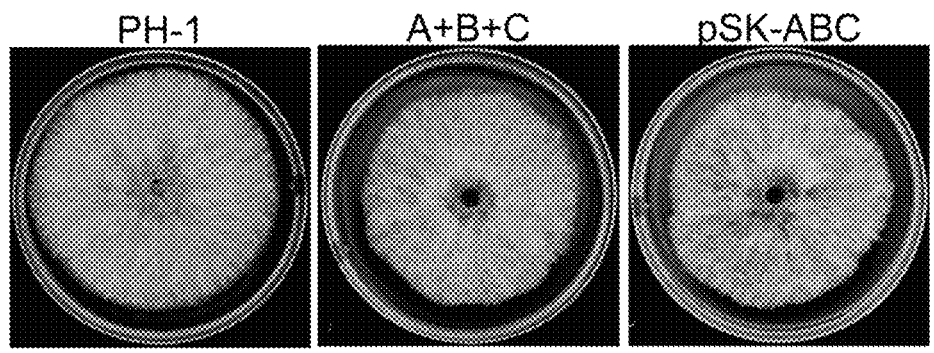
FIG. 2B shows a comparison of colony morphology of the pSK-ABC transfectant, a strain PH-1 and a strain A+B+C.
Figure 2C:
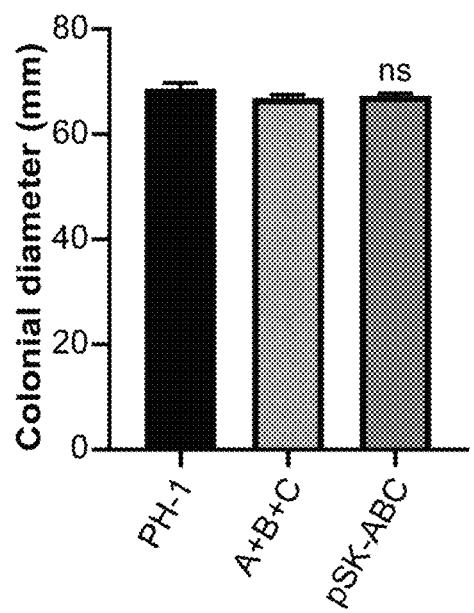
FIG. 2C shows a comparison of growth diameters of pSK-ABC transfectant, the strain PH-1 and the strain A+B+C on Potato Dextrose Agar (PDA) medium.
Figure 2D:
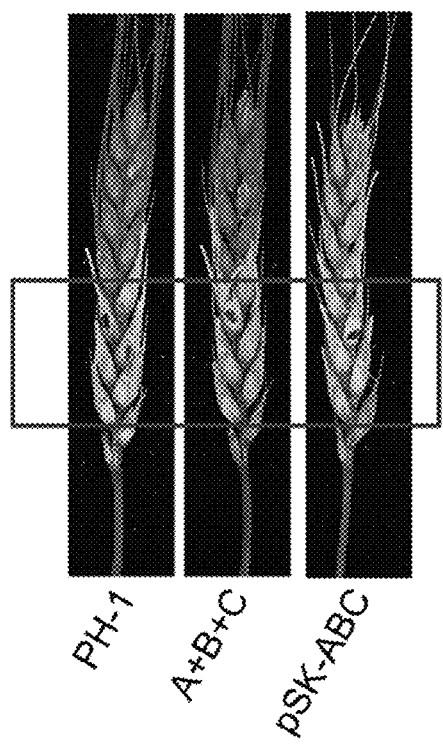
FIG. 2D shows a disease symptom of wheat spikelets when the pSK-ABC transfectant, the strain PH-1 and the strain A+B+C are inoculated onto wheat.
Figure 2E:
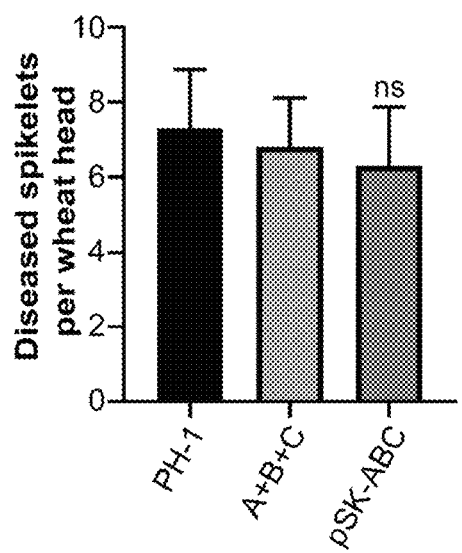
FIG. 2E shows the number of diseased spikelets per wheat head when the pSK-ABC transfectant, the strain PH-1 and the strain A+B+C are inoculated onto wheat.
Figure 3A:
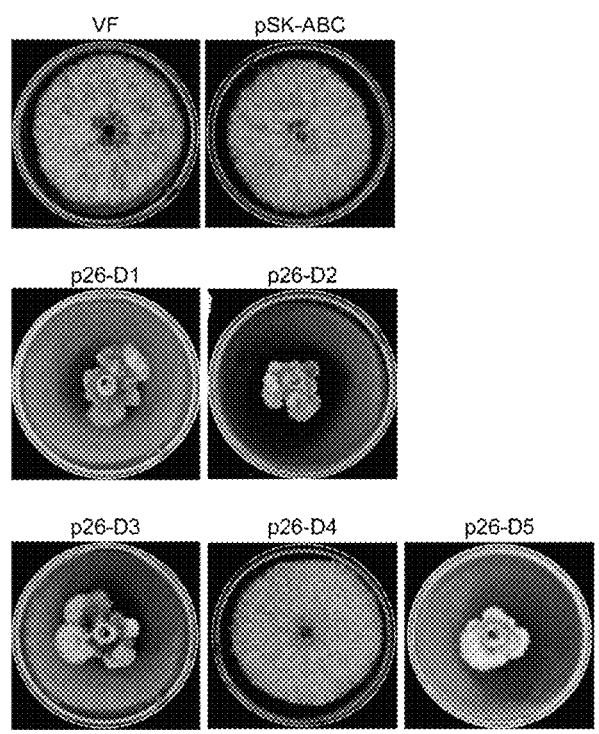
FIG. 3A is a comparison of colony morphology of deletion mutants p26-D1, p26-D2, p26-D3, p26-D4 and p26-D5, the strain pSK-ABC and a strain PH-1 (VF).
Figure 3B:
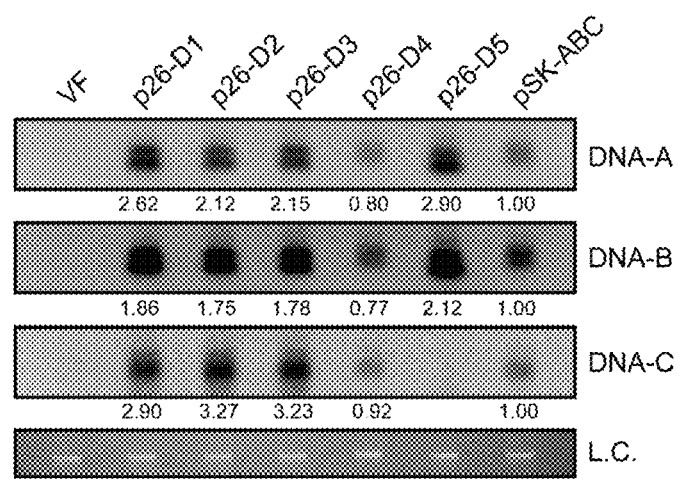
FIG. 3B shows Southern blot detection of the deletion mutants p26-D1, p26-D2, p26-D3, p26-D4 and p26-D5, the strain pSK-ABC and the strain PH-1 (VF).
Figure 3C:
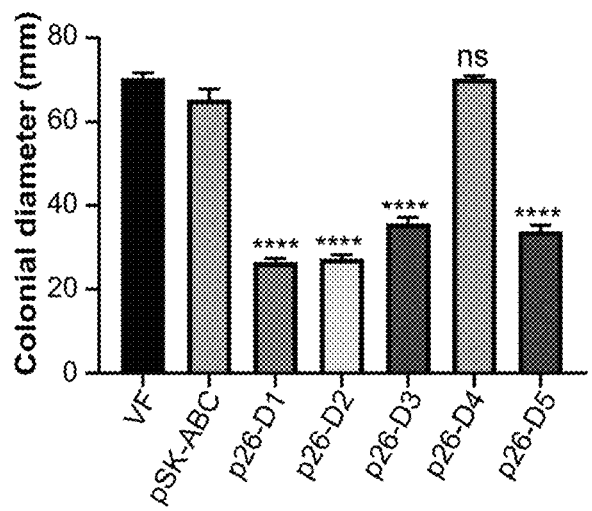
FIG. 3C shows a comparison of growth diameters of the deletion mutants p26-D1, p26-D2, p26-D3, p26-D4 and p26-D5, the strain pSK-ABC and the strain PH-1 (VF) on PDA medium.
Figure 4:
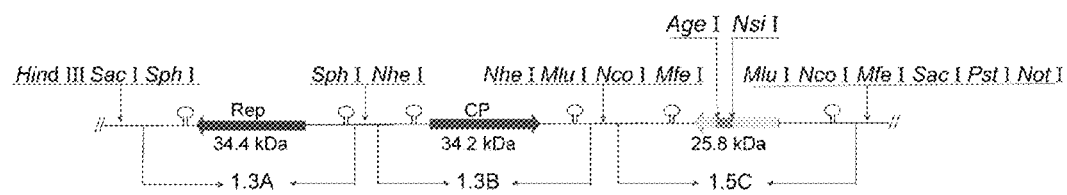
FIG. 4 is a schematic structural diagram of virus-induced gene silencing (VIGS) vector p26-D4.

Embodiment 1 Construction of an Infectious Clone pSK-ABC with Three Components of *Fusarium graminearum* DNA Virus FgGMTV1 in Series and Verification of its Infectivity 1. Construction of the Infectious Clone pSK-ABC with Three Components of DNA Virus FgGMTV1 in Series Patent CN109810997 A with a name of "Construction method of infectious clone of *Fusarium graminearum* single-stranded circular DNA virus FgGMTV1/HB58" discloses a construction method of infectious clone of *Fusarium graminearum* single-stranded DNA virus FgGMTV1/HB58, which includes DNA-A infectious clone construction, DNA-B infectious clone construction and DNA-C infectious clone construction. 2 units of DNA-A and DNA-B molecular sequences and 1.6 units of DNA-C molecular sequences are connected to the cloning vector pBluescript II SK(+) (pSK) respectively, and infectious clones pSK-2A, pSK-2B and pSK-1.6C of the three components of the virus are constructed. Because plasmids of three infectious clones transfect at the same time, and the steps are complicated, the DNA-A and DNA-B molecules herein are reduced to 1.3 units, and DNA-C molecules are reduced to 1.5 units, which only contain coding regions of the three components and two repetitive non-coding regions, respectively, and are connected in series to the vector pBluescript II SK(+). At the same time, suitable restriction enzyme sites are added at both ends of sequences of DNA-A, DNA-B and DNA-C respectively, so as to facilitate further mutant construction (see FIG. 1). Hind III (1-6nt), SacI (7-12nt), and SphI (13-18nt) restriction enzyme sites are designated at one end of DNA-A. MluI (5464-5469nt), NcoI (5470-5475nt), MfeI (5476-5481nt), SacI (5482-5487nt), PstI (5488-5493nt) and NotI (5494-5501 nt) restriction enzyme sites are designed at one end of DNA-C. The combination of Hind III (1-6nt) and NotI (5494-5501nt) is used to connect the clone to pBluescript II SK(+) cloning vector. Two restriction enzyme sites, SphI (1760-1765nt) and NheI (1766-1771nt), are designed between DNA-A and DNA-B, and four restriction enzyme sites, NheI (3509-3514nt), MluI (3515-3520nt), NcoI (3521-3526nt) and MfeI (3527-3532nt), are designed between DNA-B and DNA-C. Through the rational use of various restriction enzyme sites, the mutation of the three components of DNA-A, DNA-B and DNA-C is realized. The infectious clone sequence is synthesized by Shanghai Generay Biotechnology Co., Ltd. and connected to pBluescript II SK(+) cloning vector to obtain the infectious clone pSK-ABC. The sequence shown in the following SEQ ID NO: 1 is the complete sequence of the infectious clone pSK-ABC (without vector), with restriction enzyme sites of 1-18nt, 1760-1771nt, 3509-3532nt, 5464-5501nt. 19-1759nt is the sequence of component A, 1772-3508nt is the sequence of component B and 3533-5463nt the sequence of component C. Hind III (1-6nt) and NotI (5494-5501nt) double restriction enzyme digestion are used to connect the sequence to pBluescript II SK(+) cloning vector. SEQ ID NO: 1 is:

```
5'-

AAGCTTGAGCTCGCATGCTTCGGCGAGTTTAGTTGCGTCGAACTCATCAGGTGTTTGG

GAATAAGTGAAAAGCCATTTTTTACATCGGAGTCGGTATCTGTGATCACTAGTTAGTTA

GTTGGGAATAGCTTCACTTTTTGGCAATTGAGTTAAGTAAGGGTCATTGCACCATCAT

GGGGGAGGGACCTCCGGGGGGCCCCATGTGGGGCTGTACCCGCGTCAGAAGCCCA

AGCTCTGGAATAAAAAAATAAAAAATACGTACTGGTTGCGTTGTCGTTTTTGTGGCT

GAGGTGTTTCTGAGTCACATGATTCGGAAGCGCGTTTGGACATTGTGGCTGAAGAGT

GGCTTTGCGGAGGTCAAGAAATCTAAGAAAGAGAGGATTTAAGATTCTTCTCTTTCTT

AGATTTGTGACCGTGACCCAAGTTTGATTTATATACTAGTTATGTGTTGACTAAGGTAC

AGAGAGGGGTAGTGATCTCCACAATAATGGCGTTAGCGTCCATCCATTTCCAATCAAT

ATCAGTGCAGGTACGGCGTGGATCTTCATTGGCTATGTAGATGCACGGCTTACCCCAC

ATGACCCGCTGTTTTCCTTTGTACTTGTCGGTAGCTACGAATTCTCGTTGGCCGAACC

ATTGTTTGTAATTTGGAAAAGAGGAGAACCCACCAATCAAGTCATCAAACACCGCGT

AGTTTACGTTAGGGTGAAAGTCAGAGAGCATGAACATGCCTGGGAAGTAGGCGTGAT

TGGCTAGACTTCGCGCCCATAGAGTTTTACCGAGGCGGGAAGCGCCGAATAAAATGA

GACTTATGGGTCGGTATGATGTGTTGTTCGTGACGTAATTGTCAACCCAGTCTTTGAG

TTCGGGATAGTCAGAGTAATTGACAGTAATTTGTGGAGATTCGTATGTGCTCTGTGGT
```

-continued

```
GGACCGAATTTCCATTCAGCAAATGACTTGATGTTGTTCCAGCATTTGATGGATTGGTT

AGGTAGTTCGGTGGCAGCCAAGTGTAAAAATTCTTTTGCGGAAGTTGATTGGTCGAT

GATACGCAACCATTCTTTATCCATGTTCTTTTGGTTCAAGGATGGTTGGTGTGGGGTG

TACCCTCTTCCCATTGGATGTCGTTATCTTTTTTTACGTAATTGACGACAGTGTGTGGG

GTTCTGGTGACAACTTCGATGTTGGGGTGAACACCACAGAAATCGAAGTCCCGTGCG

TTGTTTGAAGTGTGAATAGTTTCAACTTCCCAATACACGTGATGGTGGAATCCGCCAT

CTTTGTGTTGTTCTTTTGAGATGACGAGATAGACAAGAAGTGGACTTTTTCTTTGAA

CATTTCGGCGAGTTTAGTTGCGTCGAACTCATCAGGTGTTTGGGAATAAGTGAAAAG

CCATTTTTTACATCGGAGTCGGTATCTGTGATCACTAGTTAGTTAGTTGGGAATAGCTT

CACTTTTTGGCAATTGAGTTAAGTAAGGGTCATTGCACCATCATGGGGGAGGGACCTC

CGGGGGGGCCCCATGTGGGGCTGTACCCGCGTCAGAAGCCCAAGCTCTGGAATAAA

AAAAATAAAAAATACGTACTGGTTGCGTTGTCGTTTTTGTGGCTGAGGTGTTTCTGAG

TCACATGATTCGGAAGCGCGTTTGGACATTGTGGCTGAAGAGTGGCTTTGCGGAGGT

CAAGAAATCTAAGAAAGAGAGGATTTAAGATTCTTCTCTTTCTTAGATTTGTGACCGT

GACCCAAGTTTGATTTATATACTAGGCATGC

GCTAGCGGTAATTTTAGTGTAGCAAAATTGAGTTGGTGATAGCTTCATTTTTTTGGATC

CACTTTGTGACAATTGAGTTGAAGTAAGGGTCATTGCACCATCATGGGGGAGGGACC

TCCGGGGGGCCCCATGTGGGCTGTACCCGCGTCAGAAGCCCAAGCTCCGGAATAA

AAAAAAATCAAAAGTAGACTGTCGGTTAAAGTTCGGTTGGGTAGGATTAGTCAGCAA

ATTTTCAACCAATAGCGGAGGTCAAGAAATCTAAGAAAGAGAGGATTTAAGATTCTT

CTCTTTCTTAGATTTGTGACCGTGACCCAGGTTTGATTTTGGGTATATAAGGGAGGGT

AGCCACCATTTTTGCTAGTCTGTTTTTGGACTTAAAAAATTTATTTTTTAACACAAAAC

ATTATTACGTCGACAAAAATGGCTTCTACAAAGAAGAAATCATACAACAACAAGAAG

GCTTATAAAAAAAAGAATGGAAGTCGAAGAAGACTTGGGACAAGTCTAGTTATTAC

GACAATTACCAGTCGAAGATGAATATTTCGAATATGCAGACGAAGAGGGACAACATG

ATGTGTGTGACGTCACATTGTGGTGTTCCGAATGCGGCGTTACTGGAGAATTCTGTTG

TGGGTGAAATTCCAGCCAATATGGGAGTTCATTATATTATGTGGTCTCCTACGTATCGA

GAGGCGGTACCACCGAATCGAGCGGCACAGTTGGATCGGCAATCCGCAAACACATTT

TTTACTGGTTGGAAGGATAATTTGTCCTATCAATTTAAGGGACAGATTACAGGGATTCA

CCTGAGGGTTGTGATATCTACCCGAAGAGAAGTGGAGTCCGCGCAGCCTTTTATTGG

GCCGGGGAATACGCTGTGCAGAAACTTGGCGGTTCGTGATATGTCGGATGAGACATT

GGACCAGTTTTTGTCGGGTACCCGGGATGTTGATTGGACGTTGGTGAATGTGATGGAC

ACGATGTTTGATCCGGCGGTGTGCAAGGTGTTGTTTCGGCAGAGGAAGATTTTAGGT

GCAGCTGATGCGTTGTTGAAGACGGAGGAGTTTTATCACCGTATCCGTCGGCCTATGG

TGTACGGCGATAGGCAGGATGGTTTGGAGTTTGTGTCTAGTGGTTGGGCTGGAAGGG

AGTCGGAGAACATATACGTCATTGATATGTACTCTTTGATTTCGGCAGCCCCACCGTTA

GGTAATTTGTTGGATGGAGAGGGAAATATTGTTTTGGATGACAAGAAACGGCCTATTC

CCGTATATGCGAAGTTAAATATTAGTGGAAATAGTATAGTGTATTGGAGGGAGTAGGGT

AATTTTAGTGTAGCAAAATTGAGTTGGTGATAGCTTCATTTTTTTGGATCCACTTTGTG

ACAATTGAGTTGAAGTAAGGGTCATTGCACCATCATGGGGGAGGGACCTCCGGGGGG

GCCCCATGTGGGCTGTACCCGCGTCAGAAGCCCAAGCTCCGGAATAAAAAAAAATC
```

-continued

```
AAAAGTAGACTGTCGGTTAAAGTTCGGTTGGGTAGGATTAGTCAGCAAATTTTCAAC
CAATAGCGGAGGTCAAGAAATCTAAGAAAGAGAGGATTTAAGATTCTTCTCTTTCTTA
GATTTGTGACCGTGACCCAGGTTTGATTTTGGGTATATAAGGGAGGGGTAGCCACCAT
TTTTGCTAGTCTGTTTTTGGACTTAAAAAATTTATTTTTTAACACAAAACATTATTACGT
CGACAAAAGCTAGC ACGCGT CCATGG
CAATTGCTTTATATTGTAAAAAATATTTGTAACTGTAAATAATTAGTTGGTGATAGCTTC
ATTTTTTTTACTCCACTTTGTGACAATTGAGTTAAGTAAGGGTCATTGCACCATCATGG
GGGAGGGACCTCCGGGGGGGCCCCATGTGGGGCTGTACCCGCGTCAGAAGCCCAAG
CTCTTTGTTGAGCCGAGCGCAGCGGTAATTTGGAGTCACGTGAGGTAAAATAAAATG
TGGACTTACGTTCTTGGAATTGATGATTGAGACATTTTGAAAAAGTGTTGGAGTGGTT
GGGGTATTTATGGTCAAGGACATGTTTGGTGGTGTCATTGGTTAATATAGGTACTGTCG
GTAGATAGTTGTTGCGGTTGAAGTATAATGCGTGGAGCACCGAGGTCAGAACTTTTAG
GAAAGACGATTTAAGATTCTCTTTCCTAAAAGTCTGACCGTGACTCCCTTTGGCCTTG
ACGACGTTATTGGTGGAGGATTGGAATGTTACCCGCAATTTCACGTGACATGTGGAAA
TGTGGTGACATGAAGAATTGTGGGACGGCACAATTTTAATTGGGTGGAACACAGCAG
GGTAGGATTAGGCAGAATGAGGCAGATTTAGGCAGCGGAAATTTATTTTTAAATTGGA
GCATTGTCTAAATCTAGAAGTACATGGTACCAGTCATCATCGTTTGGTTGATGATCTGG
TATGTCCACCCAATCAGGATCATTTAAATTATGTACAATTGAATTGTTATGATTTGTAAA
AAAAAAGATAGGTAATCGCATAACGTGTTTTTGTTGAATAAAATAATACACGTGTTT
GCGTATTGTTGTACCATGTCATGTGGGTCGGGATTGTTGTGGAGATGACACGTGTTAG
TGCTGGTATGAACTCGCAGGAGTGTAGTACCAGTCGACAAAGGCTTGGATGTGTTGG
CGGTGTCGTTGGAGTAGTGTAGGGTGAGTTTCCTCGAAACGACTAAGAAACGCCCCT
TGATTTGGCTCGGAGAAAAGTTGTTGCCAGAAGGGGTCAGATGTGGCTGAGCAAAG
ATCTGCATCCCCGAACTGAGCCACAAGCACCTCTTTAGACTGGATGCTCTCGTATACC
GGGCCTGCATGTGTGTATATTGGCAGAATAGAAGGCATAACTCCGCTGTAAGCGAGTT
GTAGGCTTCGTTGGAGGGGAATGTTTCCAGTATCGATGTAGATATCGAGATCACAGTT
CCCATTAGTTCTTGTATTGTAACCGGCGATGAATCTCTTTGGATTGATGTCCATTTGGA
GTTGAGAAGTGAAATTATCTGATTGTTTTGGGTCGACATCTTTATATTGTAAAAAATAT
TTGTAACTGTAAATAATTAGTTGGTGATAGCTTCATTTTTTTTACTCCACTTTGTGACAA
TTGAGTTAAGTAAGGGTCATTGCACCATCATGGGGGAGGGACCTCCGGGGGGCCCC
ATGTGGGGCTGTACCCGCGTCAGAAGCCCAAGCTCTTTGTTGAGCCGAGCGCAGCGG
TAATTTGGAGTCACGTGAGGTAAAATAAATGTGGACTTACGTTCTTGGAATTGATGA
TTGAGACATTTTGAAAAAGTGTTGGAGTGGTTGGGGTATTTATGGTCAAGGACATGTT
TGGTGGTGTCATTGGTTAATATAGGTACTGTCGGTAGATAGTTGTTGCGGTTGAAGTAT
AATGCGTGGAGCACCGAGGTCAGAACTTTTAGGAAAGACGATTTAAGATTCTCTTTC
CTAAAAGTCTGACCGTGACTCCCTTTGGCCTTGACGACGTTATTGGTGGAGGATTGGA
ATGTTACCCGCAATTTCACGTGACATGTGGAAATGTGGTGACATGAAGAATTGTGGGA
CGGCACAATTTTAATTGGGTGGAACACAGCAGGGTAGGATTAGGCAGAATGAGGCAG
ATTTAGGCAGCGGAAATTTATTTACGCGT CCATGG CAATTG GAGCTC CTGCAG
GCGGCCGC-3'.
```

2. Protoplast Preparation of *Fusarium graminearum*

*Fusarium graminearum* strain PH-1 on PDA plate is inoculated into a 250 mL triangular flask with 100 mL carboxylmethyl cellulose (CMC) liquid medium, and cultured for 3-5 days at 25° C. and 180 rpm (preferably 4 days); the culture medium is filtered with sterilized three-layer lens-wiping paper, centrifuged at 4000 rpm for 5 min at room temperature, and the supernatant is discarded; sterilized water is added, conidia precipitation is resuspended and diluted to the concentration of $10^7$ spores/mL; $3\times10^7$ spores are transferred to a 250 mL triangular flask containing 100 mL Yeast Extract Peptone Dextrose (YEPD) liquid medium, and shaken at 25° C. and 180 rpm for 12-14 h; the overnight culture medium is filtered with three-layer sterilized lens-wiping paper, rinsed with sterile water for three times, then rinsed with 1 M sucrose for two times, drained with sterilized filter paper, and mycelium is collected; mycelium is transferred to 20 mL of protoplast hydrolysate with a sterile tweezers, gently shaken at 90 rpm and 28° C. for 2-3 h, and the protoplast granules are examined in terms of quantity by microscope every 0.5 h; the enzymolysis mixture is filtered with two-layer sterilized lens-wiping paper into a sterile 50 mL centrifuge tube, and rinsed twice with 1 M sucrose solution to rinse off as many protoplasts as possible: the protoplasts are centrifuged at 2600 rpm at 4° C. for 1 min, the supernatant is discarded, the protoplast are resuspended with Sucrose-Tris-Calcium (STC) buffer (1 M sorbitol, 50 mM Tris-HCl pH 8.0, and 50 mM $CaCl_2\cdot2H_2O$) precooled on ice, and the protoplast are washed for three times according to the above centrifugation conditions: finally, the protoplasts are resuspended with STC buffer, and the final concentration of the protoplasts is adjusted to $2\times10^7$ cells/mL, the protoplasts are sub-packaged at 200 μL/tube, added with dimethyl sulfoxide (DMSO) with final concentration of 7%, mixed well and stored at −80° C.

3. Polyethylene Glycol (PEG)-Mediated Transfection of pSK-ABC

The protoplasts are taken out at −80° C. and thawed on ice: 200 μL PH-1 protoplasts and 30 μg plasmid are added into a 2 mL centrifuge tube, mixed gently, and placed on ice for 20 min; 1.25 mL PEG-Tris-Calcium (PTC) buffer (STC buffer containing 40% PEG 4000) is dripped into the 2 mL centrifuge tube, mixed with a gun head, and then allowed to stand at room temperature for 20 min. The protoplasts in the 2 mL centrifuge tube are transferred into the 15 mL centrifuge tube, the 2 mL centrifuge tube is rinsed repeatedly with 5 mL Terrific Broth 3 (TB3) (3 g Yeast Extract, 3 g Casamino Acids, 200 g Sucrose, added with distilled water to constant volume to 1 L) (containing 50 μg/mL ampicillin), then added into the above 15 mL centrifuge tube, shaken lightly at 25° C. and 90 rpm overnight (16 h): the regenerated substance of protoplasts are centrifuged at 4000 rpm for 5 min, the supernatant is discarded, 600 μL STC is added to resuspend and precipitate, 200 μL of the protoplasts are taken respectively in turn and put in the center of a 9 cm culture dish, and added with 20 mL of TB3 solid medium containing 50 μg/mL ampicillin: the plate is placed with face upward, and cultured overnight at 25° C. in the dark. The next day, the plate is tilted to remove STC floating on the surface, and cultured for 5 days. The morphology of mycelium is observed, small pieces of myceliums is cut from different positions on the edge and transferred to PDA plate, cultured, and further experimental observation is conducted after molecular identification.

4. Determination of Colony Morphology and Growth Rate of the Strains

The mycelian blocks of transfectant strain are punched with a 5 mm punch and placed in the center of PDA medium plate to activate the strain. A 5 mm punch is used to punch the blocks on the edge of the colony of the activated strain, and the blocks are transferred to the center of the PDA medium plate, and 5 repetitions are conducted respectively. After 4 days of dark culture at 25° C., the colony morphology and diameter are observed and statistically analyzed.

5. Determination of Pathogenicity of the Strains

Yangmai 158, a wheat variety, is planted and used for wheat spikelet inoculation when the wheat grows to the flowering stage. The conidia of each transfectant strain are prepared according to the above method, and the spore concentration is measured by blood cell counting plate, and then the spore concentration is adjusted to $3\times10^5$ spores/mL. Spikelets with basically the same growth are selected, and when the fifth spikelet is found from bottom to top, the inner glume from the outer glume are separated with fingers. 10 μL of the prepared spore solution is sucked and injected into the root between the inner glume and the outer glume, and spikelet is gently closed to keep a natural state. The inoculated spikelet is marked with a marker and a label is put on the wheat stalk, and the inoculation strain, inoculation method, inoculation date, inoculator and other information are recorded. Each strain is inoculated onto at least 15 spikelets, subjected to moisturizing culture with fresh-keeping bag for 48 h: after taking off the fresh-keeping bag, each strain is cultured for 14 days, the symptom of wheat spikelets is observed, and the number of diseased spikelets per wheat head is counted.

6. Results

FIG. 2A, FIG. 2B, FIG. 2C, FIG. 2D, and FIG. 2E show an infection activity analysis of an infectious clone pSK-ABC of FgGMTV1 with three components connected in series. The results show that the pSK-ABC transfectant strain is obtained through protoplast preparation, transfection and regeneration. By Southern blot analysis (see FIG. 2A), it is confirmed that the virus exists in the infectious clone pSK-ABC transfectant strain, and there is no significant difference in colony morphology, colony growth rate and pathogenicity between the pSK-ABC transfectant strain and the strain A+B+C co-transfected by infectious clones of three components (see FIG. 2B-FIG. 2E). It is confirmed that the infectious clone pSK-ABC with three components of DNA virus FgGMTV1 in series is successfully constructed.

Embodiment 2 Construction of Gene Silencing Vector p26-D4 Based on Virus FgGMTV1

1. Design and Construction of Gene Silencing Vector Based on FgGMTV1

Based on the infectious clone pSK-ABC, the p26 coding frame of DNA-C component is deleted with the length of 150nt in turn, and five deletion mutants are obtained, named p26-D1, p26-D2, p26-D3 and p26-D4, and p26-D5. The p26-D5 is deleted by 81nt. The method of constructing these mutants is completed by KOD-Plus-Mutagenesis Kit (code NO. SMK-101) of Toyobo Life Science company. The experimental principle of the kit is that by using pSK-ABC as a template through inverse PCR method, two primers are designed in the opposite direction, and restriction enzyme sites NsiI and AgeI are introduced at the same time, and the plasmid is subjected to complete PCR by using high-fidelity KOD-Plus-enzyme, and finally the target mutants are obtained by screening.

The deletion mutants based on DNA-C are constructed by designing specific primers, as shown in Table 1, in which the underlined sequences are introduced restriction enzyme sites NsiI and AgeI.

TABLE 1

DNA-C mutant primers

| Primer name | Primer sequence (5'-3') |
|---|---|
| p26-D1-F (SEQ ID NO: 8) | AGGATGCATTACAACTCGCTTACAGCGGAGTTATGCC TT |
| p26-D1-R (SEQ ID NO: 9) | AGGACCGGTCATCTTTATATTGTAAAAAATATTTGTAA C |
| p26-D2-F (SEQ ID NO: 10) | AGGATGCATAACAACTTTTCTCCGAGCCAAATCAAG GGG |
| p26-D2-R (SEQ ID NO: 11) | AGGACCGGTGGCTTCGTTGGAGGGGAATGTTTCCAG TAT |
| p26-D3-F (SEQ ID NO: 12) | AGGATGCATCATCTCCACAACAATCCCGACCCACATG AC |
| p26-D3-R (SEQ ID NO: 13) | AGGACCGGTGCCAGAAGGGGTCAGATGTGGCTGAG CAAA |
| p26-D4-F (SEQ ID NO: 14) | AGGATGCATGATTGGGTGGACATACCAGATCATCAAC CA |
| p26-D4-R (SEQ ID NO: 15) | AGGACCGGTACACGTGTTAGTGCTGGTATGAACTCG CAG |
| p26-D5-F (SEQ ID NO: 16) | AGGATGCATTAAAAATAAATTTCCGCTGCCTAAATCT GC |
| p26-D5-R (SEQ ID NO: 17) | AGGACCGGTAGGATCATTTAAATTATGTACAATTGAA TT |

Protoplast preparation of *Fusarium graminearum*, transfection of virus deletion mutants mediated by PEG and observation of colony morphology of the strains are all the same as those in Embodiment 1.

FIG. 3A, FIG. 3B, and FIG. 3C illustrate an analysis of infection activity of deletion mutant based on DNA-C. The results show that five deletion mutants p26-D1, p26-D2, p26-D3, p26-D4 and p26-D5 are constructed based on the infectious clone pSK-ABC. It is confirmed by Southern blot that three components of the mutants p26-D1, p26-D2, p26-D3 and p26-D4 could be effectively replicated, but only p26-D4 has the same phenotype as the wild-type virus, that is, the infection of mutant virus would not cause abnormal phenotype of the host (FIG. 3A, FIG. 3B, FIG. 3C). p26-D4 may be used as a candidate gene silencing vector, named p26-D4, that is, the sequence of 284-434nt of the coding protein p26 of the DNA-C component is deleted, and the restriction enzyme sites NsiI and AgeI are introduced, the structure of the VIGS vector p26-D4 is shown in FIG. 4.

The complete sequence (without vector) of the VIGS vector p26-D4 is shown in SEQ ID NO: 2, with the restriction enzyme sites of 1-18nt, 1760-1771nt, 3509-3532nt, 4239-4256nt, 5332-5369nt. 19-1759nt is the sequence of component A, 1772-3508nt is the sequence of component B and 3533-4238nt, 4257-5331nt is the sequence of component C. Hind III (1-6nt) and NotI (5362-5369nt) are used to connect the sequence to pBluescript II SK(+) cloning vector. NsiI (4239-4244nt) and AgeI (4251-4256nt) are used to insert foreign gene fragments. SEQ ID NO: 2 is:

5'-AAGCTT GAGCTC

GCATGCTTCGGCGAGTTTAGTTGCGTCGAACTCATCAGGTGTTTGGGAATAAGTGAA

AAGCCATTTTTTACATCGGAGTCGGTATCTGTGATCACTAGTTAGTTAGTTGGGAATAG

CTTCACTTTTTGGCAATTGAGTTAAGTAAGGGTCATTGCACCATCATGGGGGAGGGAC

CTCCGGGGGGGCCCCATGTGGGGCTGTACCCGCGTCAGAAGCCCAAGCTCTGGAATA

AAAAAAATAAAAAATACGTACTGGTTGCGTTGTCGTTTTTGTGGCTGAGGTGTTTCTG

AGTCACATGATTCGGAAGCGCGTTTGGACATTGTGGCTGAAGAGTGGCTTTGCGGAG

GTCAAGAAATCTAAGAAAGAGAGGATTTAAGATTCTTCTCTTTCTTAGATTTGTGACC

GTGACCCAAGTTTGATTTATATACTAGTTATGTGTTGACTAAGGTACAGAGAGGGGTA

-continued

```
GTGATCTCCACAATAATGGCGTTAGCGTCCATCCATTTCCAATCAATATCAGTGCAGGT

ACGGCGTGGATCTTCATTGGCTATGTAGATGCACGGCTTACCCCACATGACCCGCTGT

TTTCCTTTGTACTTGTCGGTAGCTACGAATTCTCGTTGGCCGAACCATTGTTTGTAATT

TGGAAAAGAGGAGAACCCACCAATCAAGTCATCAAACACCGCGTAGTTTACGTTAGG

GTGAAAGTCAGAGAGCATGAACATGCCTGGGAAGTAGGCGTGATTGGCTAGACTTCG

CGCCCATAGAGTTTTACCGAGGCGGGAAGCGCCGAATAAAATGAGACTTATGGGTCG

GTATGATGTGTTGTTCGTGACGTAATTGTCAACCCAGTCTTTGAGTTCGGGATAGTCA

GAGTAATTGACAGTAATTTGTGGAGATTCGTATGTGCTCTGTGGTGGACCGAATTTCC

ATTCAGCAAATGACTTGATGTTGTTCCAGCATTTGATGGATTGGTTAGGTAGTTCGGTG

GCAGCCAAGTGTAAAAATTCTTTTGCGGAAGTTGATTGGTCGATGATACGCAACCATT

CTTTATCCATGTTCTTTTGGTTCAAGGATGGTTGGTGTGGGGGTGTACCCTCTTCCCAT

TGGATGTCGTTATCTTTTTTTACGTAATTGACGACAGTGTGTGGGGTTCTGGTGACAA

CTTCGATGTTGGGGTGAACACCACAGAAATCGAAGTCCCGTGCGTTGTTTGAAGTGT

GAATAGTTTCAACTTCCCAATACACGTGATGGTGGAATCCGCCATCTTTGTGTTGTTCT

TTTGAGATGACGAGATAGACAAGAAGTGGACTTTTTTCTTTGAACATTTCGGCGAGTT

TAGTTGCGTCGAACTCATCAGGTGTTTGGGAATAAGTGAAAAGCCATTTTTTACATCG

GAGTCGGTATCTGTGATCACTAGTTAGTTAGTTGGGAATAGCTTCACTTTTTGGCAATT

GAGTTAAGTAAGGGTCATTGCACCATCATGGGGGAGGGACCTCCGGGGGGGCCCCAT

GTGGGGCTGTACCCGCGTCAGAAGCCCAAGCTCTGGAATAAAAAAAATAAAAAATAC

GTACTGGTTGCGTTGTCGTTTTTGTGGCTGAGGTGTTTCTGAGTCACATGATTCGGAA

GCGCGTTTGGACATTGTGGCTGAAGAGTGGCTTTGCGGAGGTCAAGAAATCTAAGAA

AGAGAGGATTTAAGATTCTTCTCTTTCTTAGATTTGTGACCGTGACCCAAGTTTGATTT

ATATACTAGGCATGCGCTAGCGGTAATTTTAGTGTAGCAAAATTGAGTTGGTGATAGCT

TCATTTTTTTGGATCCACTTTGTGACAATTGAGTTGAAGTAAGGGTCATTGCACCATCA

TGGGGGAGGGACCTCCGGGGGGGCCCCATGTGGGGCTGTACCCGCGTCAGAAGCCC

AAGCTCCGGAATAAAAAAAAATCAAAAGTAGACTGTCGGTTAAAGTTCGGTTGGGTA

GGATTAGTCAGCAAATTTTCAACCAATAGCGGAGGTCAAGAAATCTAAGAAAGAGAG

GATTTAAGATTCTTCTCTTTCTTAGATTTGTGACCGTGACCCAGGTTTGATTTGGGTA

TATAAGGGAGGGGTAGCCACCATTTTTGCTAGTCTGTTTTTGGACTTAAAAAATTTATT

TTTTAACACAAAACATTATTACGTCGACAAAAATGGCTTCTACAAAGAAGAAATCATA

CAACAACAAGAAGGCTTATAAAAAAAAAGAATGGAAGTCGAAGAAGACTTGGGACA

AGTCTAGTTATTACGACAATTACCAGTCGAAGATGAATATTTCGAATATGCAGACGAA

GAGGGACAACATGATGTGTGTGACGTCACATTGTGGTGTTCCGAATGCGGCGTTACT

GGAGAATTCTGTTGTGGGTGAAATTCCAGCCAATATGGGAGTTCATTATATTATGTGGT

CTCCTACGTATCGAGAGGCGGTACCACCGAATCGAGCGGCACAGTTGGATCGGCAAT

CCGCAAACACATTTTTTACTGGTTGGAAGGATAATTTGTCCTATCAATTTAAGGGACA

GATTACAGGGATTCACCTGAGGGTTGTGATATCTACCCGAAGAGAAGTGGAGTCCGC

GCAGCCTTTTATTGGGCCGGGGAATACGCTGTGCAGAAACTTGGCGGTTCGTGATATG

TCGGATGAGACATTGGACCAGTTTTTGTCGGGTACCCGGGATGTTGATTGGACGTTGG

TGAATGTGATGGACACGATGTTTGATCCGGCGGTGTGCAAGGTGTTGTTTCGGCAGA

GGAAGATTTTAGGTGCAGCTGATGCGTTGTTGAAGACGGAGGAGTTTTATCACCGTAT
```

-continued

```
CCGTCGGCCTATGGTGTACGGCGATAGGCAGGATGGTTTGGAGTTTGTGTCTAGTGGT

TGGGCTGGAAGGGAGTCGGAGAACATATACGTCATTGATATGTACTCTTTGATTTCGG

CAGCCCCACCGTTAGGTAATTTGTTGGATGGAGAGGGAAATATTGTTTTGGATGACAA

GAAACGGCCTATTCCCGTATATGCGAAGTTAAATATTAGTGGAAATAGTATAGTGTATT

GGAGGGAGTAGGGTAATTTTAGTGTAGCAAAATTGAGTTGGTGATAGCTTCATTTTTT

TGGATCCACTTTGTGACAATTGAGTTGAAGTAAGGGTCATTGCACCATCATGGGGGAG

GGACCTCCGGGGGGCCCCATGTGGGCTGTACCCGCGTCAGAAGCCCAAGCTCCG

GAATAAAAAAAATCAAAGTAGACTGTCGGTTAAAGTTCGGTTGGGTAGGATTAGT

CAGCAAATTTTCAACCAATAGCGGAGGTCAAGAAATCTAAGAAAGAGAGGATTTAAG

ATTCTTCTCTTTCTTAGATTTGTGACCGTGACCCAGGTTTGATTTTGGGTATATAAGGG

AGGGGTAGCCACCATTTTTGCTAGTCTGTTTTTGGACTTAAAAAATTTATTTTTTAACA

CAAAACATTATTACGTCGACAAAAGCTAGCACGCGTCCATGGCAATTGCTTTATATTGT

AAAAAATATTTGTAACTGTAAATAATTAGTTGGTGATAGCTTCATTTTTTTTACTCCACT

TTGTGACAATTGAGTTAAGTAAGGGTCATTGCACCATCATGGGGGAGGGACCTCCGG

GGGGGCCCCATGTGGGCTGTACCCGCGTCAGAAGCCCAAGCTCTTTGTTGAGCCGA

GCGCAGCGGTAATTTGGAGTCACGTGAGGTAAAATAAAATGTGGACTTACGTTCTTG

GAATTGATGATTGAGACATTTTGAAAAAGTGTTGGAGTGGTTGGGGTATTTATGGTCA

AGGACATGTTTGGTGGTGTCATTGGTTAATATAGGTACTGTCGGTAGATAGTTGTTGCG

GTTGAAGTATAATGCGTGGAGCACCGAGGTCAGAACTTTTAGGAAAGACGATTTAAG

ATTCTCTTTCCTAAAAGTCTGACCGTGACTCCCTTTGGCCTTGACGACGTTATTGGTG

GAGGATTGGAATGTTACCCGCAATTTCACGTGACATGTGGAAATGTGGTGACATGAA

GAATTGTGGGACGGCACAATTTTAATTGGGTGGAACACAGCAGGGTAGGATTAGGCA

GAATGAGGCAGATTTAGGCAGCGGAAATTTATTTTTAAATTGGAGCATTGTCTAAATCT

AGAAGTACATGGTACCAGTCATCATCGTTTGGTTGATGATCTGGTATGTCCACCCAATC

ATGCATCCTAGGACCGGTACACGTGTTAGTGCTGGTATGAACTCGCAGGAGTGTAGTA

CCAGTCGACAAAGGCTTGGATGTGTTGGCGGTGTCGTTGGAGTAGTGTAGGGTGAGT

TTCCTCGAAACGACTAAGAAACGCCCCTTGATTTGGCTCGGAGAAAAGTTGTTGCCA

GAAGGGGTCAGATGTGGCTGAGCAAAGATCTGCATCCCCGAACTGAGCCACAAGCA

CCTCTTTAGACTGGATGCTCTCGTATACCGGGCCTGCATGTGTGTATATTGGCAGAATA

GAAGGCATAACTCCGCTGTAAGCGAGTTGTAGGCTTCGTTGGAGGGGAATGTTTCCA

GTATCGATGTAGATATCGAGATCACAGTTCCCATTAGTTCTTGTATTGTAACCGGCGAT

GAATCTCTTTGGATTGATGTCCATTTGGAGTTGAGAAGTGAAATTATCTGATTGTTTTG

GGTCGACATCTTTATATTGTAAAAAATATTTGTAACTGTAAATAATTAGTTGGTGATAGC

TTCATTTTTTTACTCCACTTTGTGACAATTGAGTTAAGTAAGGGTCATTGCACCATCA

TGGGGGAGGGACCTCCGGGGGGCCCCATGTGGGCTGTACCCGCGTCAGAAGCCC

AAGCTCTTTGTTGAGCCGAGCGCAGCGGTAATTTGGAGTCACGTGAGGTAAAATAAA

ATGTGGACTTACGTTCTTGGAATTGATGATTGAGACATTTTGAAAAAGTGTTGGAGTG

GTTGGGGTATTTATGGTCAAGGACATGTTTGGTGGTGTCATTGGTTAATATAGGTACTG

TCGGTAGATAGTTGTTGCGGTTGAAGTATAATGCGTGGAGCACCGAGGTCAGAACTTT

TAGGAAAGACGATTTAAGATTCTCTTTCCTAAAAGTCTGACCGTGACTCCCTTTGGCC
```

-continued

```
TTGACGACGTTATTGGTGGAGGATTGGAATGTTACCCGCAATTTCACGTGACATGTGG

AAATGTGGTGACATGAAGAATTGTGGGACGGCACAATTTTAATTGGGTGGAACACAG

CAGGGTAGGATTAGGCAGAATGAGGCAGATTTAGGCAGCGGAAATTTATTTACGCGTC

CATGGCAATTGGAGCTCCTGCAG GCGGCCGC-3'.
```

Embodiment 3 Silencing Effect of p26-D4

In this embodiment, GFP gene genetically expressed by Fusarium graminearum PH-1 is used as the target gene to illustrate the silencing effect of p26-D4.

1. Construction of Gene Silencing Vector Based on p26-D4

Based on p26-D4 vector, as for the target gene GFP, VIGS vector containing different fragments of GFP gene is constructed to verify the silencing effect and the size range of exogenous fragment insertion. Eight vectors are constructed: p26-D4-GFP75F, p26-D4-GFP75R, p26-D4-GFP150F, p26-D4-GFP150R, p26-D4-GFP300F, p26-D4-GFP300R, p26-D4-GFP450F and p26-D4-GFP450R. The specific construction method is to amplify GFP gene fragments with different lengths and directions by RCR method, connect the amplified fragments to p26-D4 vector by T4 DNA ligase, and finally screen the target silencing vector.

GFP gene fragments with different lengths and directions are amplified by specific primers, and the specific primers are shown in Table 2.

TABLE 2

Primers for construction of GFP gene silencing vector based on p26-D4

| Primer name | Primer sequence (5'-3') |
| --- | --- |
| p26-D4-GFP75F-F (SEQ ID NO: 18) | CCCACCGGTCAGCACGACTTCTTC |
| p26-D4-GFP75F-R (SEQ ID NO: 19) | CCAATGCATGCCGTCGTCCTTGAAG |
| p26-D4-GFP75R-F (SEQ ID NO: 20) | CCCACCGGTGCCGTCGTCCTTGAAG |
| p26-D4-GFP75R-R (SEQ ID NO: 21) | CCAATGCATCAGCACGACTTCTTC |
| p26-D4-GFP150F-F (SEQ ID NO: 22) | CCCACCGGTATGGTGAGCAAGGGCGAG |
| p26-D4-GFP150F-R (SEQ ID NO: 23) | CCAATGCATGGTGCAGATGAACTTC |
| p26-D4-GFP150R-F (SEQ ID NO: 24) | CCCACCGGTGGTGCAGATGAACTTC |
| p26-D4-GFP150R-R (SEQ ID NO: 25) | CCAATGCATATGGTGAGCAAGGGCGAG |
| p26-D4-GFP300F-F (SEQ ID NO: 26) | CCCACCGGTCAGCACGACTTCTTCAAG |
| p26-D4-GFP300F-R (SEQ ID NO: 27) | CCAATGCATGGCGAGCTGCACGCTG |
| p26-D4-GFP300R-F (SEQ ID NO: 28) | CCCACCGGTGGCGAGCTGCACGCTGC |
| p26-D4-GFP300R-R (SEQ ID NO: 29) | CCAATGCATCAGCACGACTTCTTCAAG |
| p26-D4-GFP450F-F (SEQ ID NO: 30) | CCCACCGGTATGGTGAGCAAGGGCGAG |

TABLE 2-continued

Primers for construction of GFP gene silencing vector based on p26-D4

| Primer name | Primer sequence (5'-3') |
| --- | --- |
| p26-D4-GFP450F-R (SEQ ID NO: 31) | CCAGTTGTGGCTGTTGTAGTTGTAC |
| p26-D4-GFP450R-F (SEQ ID NO: 32) | CCCACCGGTGTTGTGGCTGTTGTAG |
| p26-D4-GFP450R-R (SEQ ID NO: 33) | CCAATGCATATGGTGAGCAAGGGCGAG |

The protoplast preparation of Fusarium graminearum, PEG-mediated transfection of p26-D4-based gene silencing vector and observation of colony morphology of strains are all the same as those in Embodiment 1.

2. Fluorescence Observation

A PDA plate with cellophane is prepared, laid with a sterile cover glass, a 3 mm fresh mycelian block is placed at a distance of 2 cm from the cover glass, and cultured in the dark for 2 days. The fluorescence is observed when the mycelium grows to one third of the cover glass position. The fluorescence intensity is analyzed by ImageJ software.

3. Results

Figure 5A:
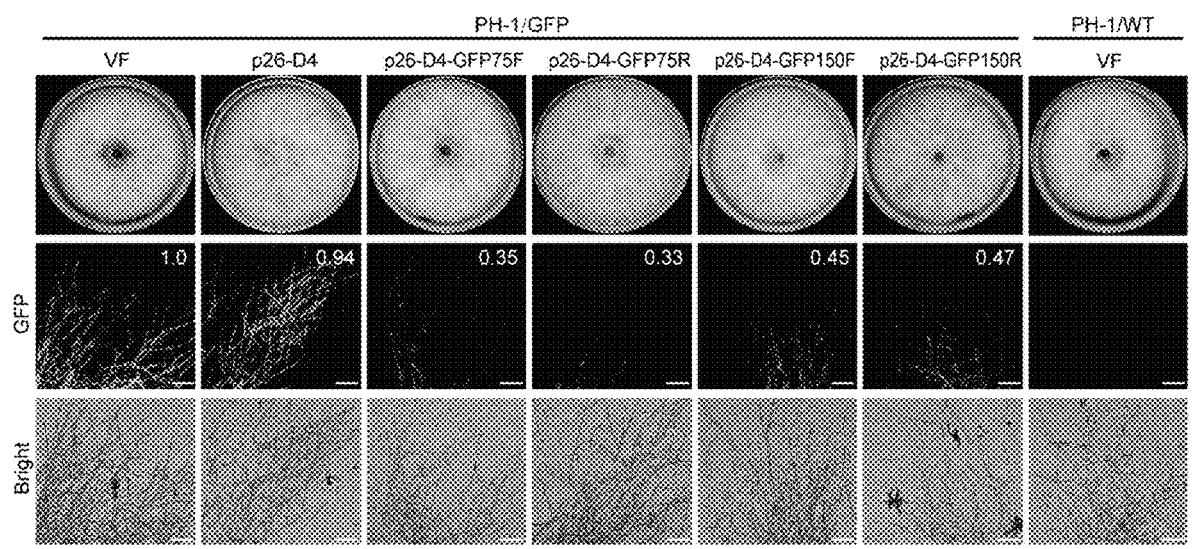
FIG. 5A is a comparison of colony morphology, fluorescence observation and intensity analysis of a strain PH-1/WT (VF), a strain PH-1/GFP (VF) and strains infected by p26-D4, p26-D4-GFP75F, p26-D4-GFP75R, p26-D4-GFP150F and p26-D4-GFP150R.
Figure 5B:
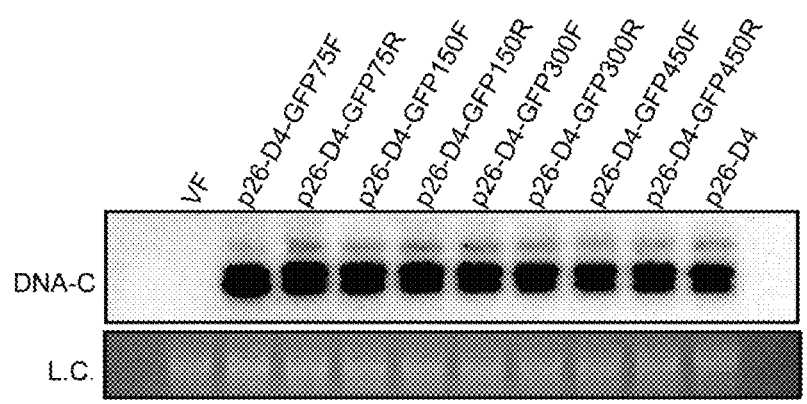
FIG. 5B shows Southern blot detection of the stain PH-1/GFP (VF) and the strains infected by p26-D4, p26-D4-GFP75F, p26-D4-GFP75R, p26-D4-GFP150F, p26-D4-GFP150R, p26-D4-GFP300F, p26-D4-GFP300R, p26-D4-GFP450F and p26-D4-GFP450R.
Figure 5C:
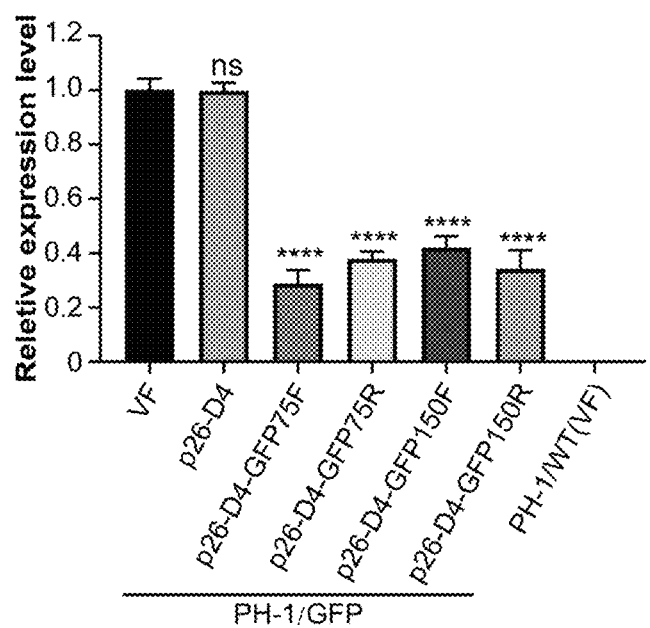
FIG. 5C shows a comparison of GFP gene expression levels of the strains PH-1/WT (VF), PH-1/GFP (VF) and the strains infected by p26-D4, p26-D4-GFP75F, p26-D4-GFP75R, p26-D4-GFP150F and p26-D4-GFP150R.
Figure 6A:
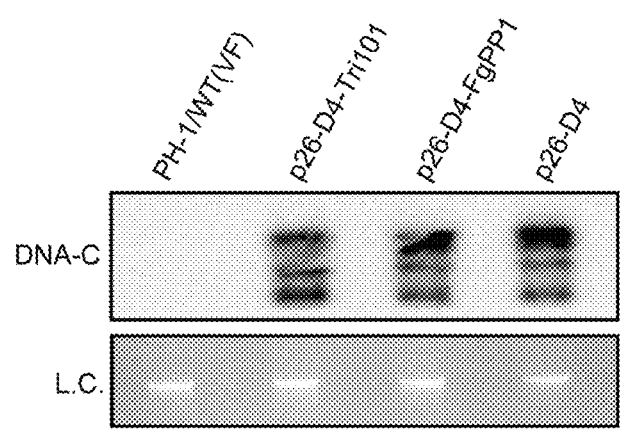
FIG. 6A shows Southern blot detection of the strain PH-1/WT (VF), and the strains infected by p26-D4, p26-D4-Tri101 and p26-D4-FgPP1.
Figure 6B:
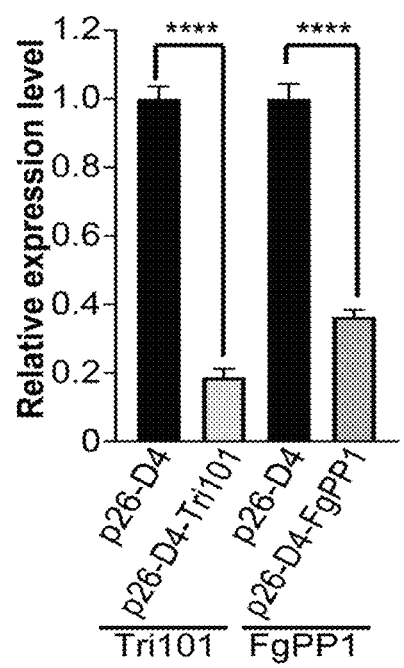
FIG. 6B shows a comparison of relative expression levels of Tri101 and FgPP1 genes in strains infected by p26-D4, p26-D4-Tri101 and p26-D4-FgPP1.
Figure 6C:
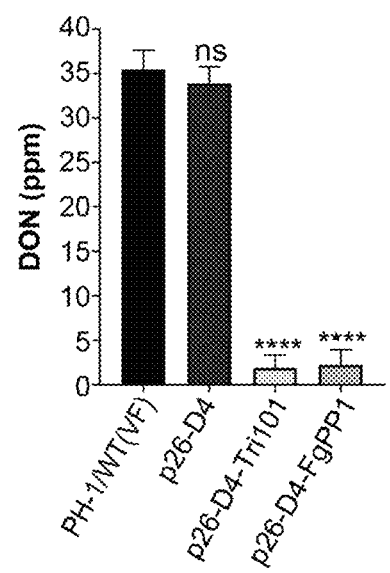
FIG. 6C shows a comparison of deoxynivaleno (DON) production induced by TBI-induced toxin-producing liquid medium among the strains infected by p26-D4, p26-D4-Tri101 and p26-D4-FgPP1.
Figure 6D:
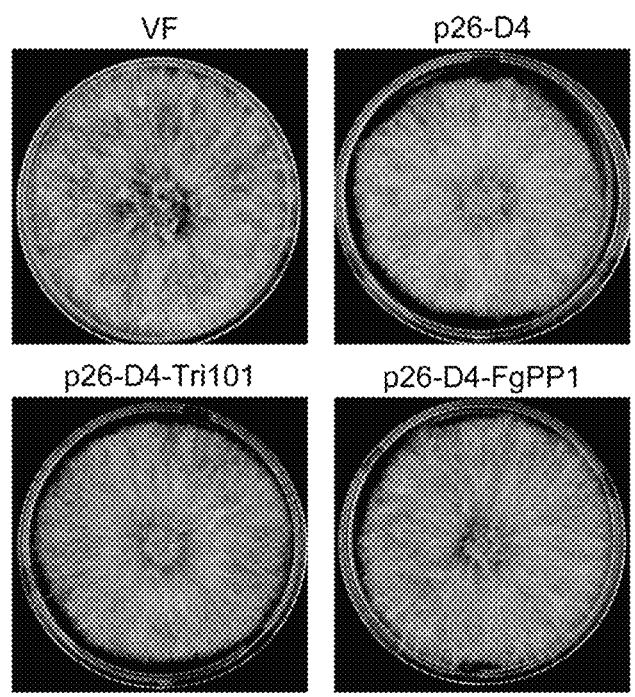
FIG. 6D shows a comparison of colony morphology of the strain PH-1/WT (VF), and the strains infected by p26-D4, p26-D4-Tri101 and p26-D4-FgPP1.
Figure 6E:
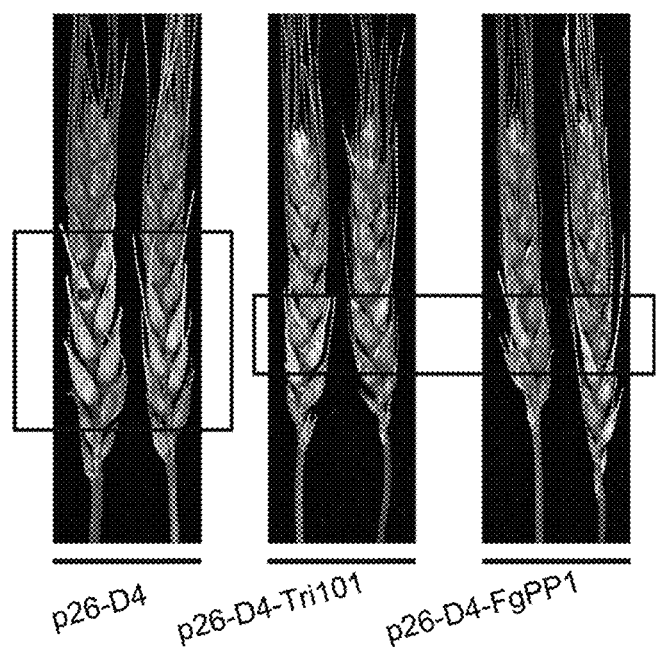
FIG. 6E shows disease symptom of wheat spikelets after strains infected by p26-D4, p26-D4-Tri101 and p26-D4-FgPP1 are inoculated onto wheat.
Figure 6F:
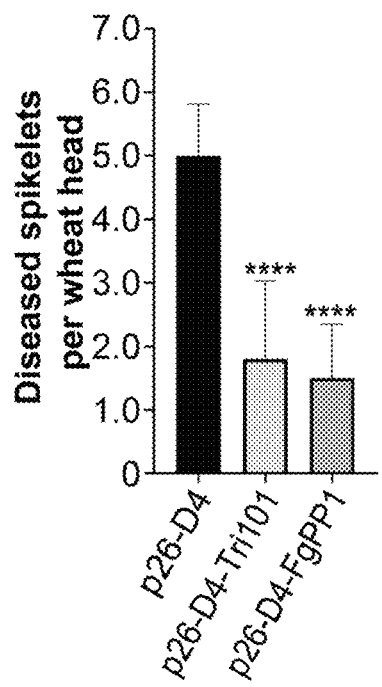
FIG. 6F shows the number of diseased spikelets per wheat head after strains infected by p26-D4, p26-D4-Tri101 and p26-D4-FgPP1 are inoculated onto wheat.
Figure 7A:
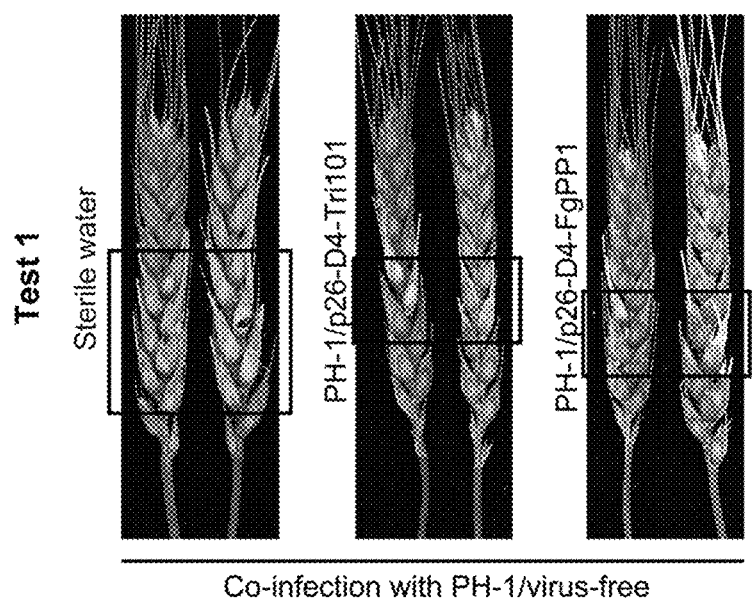
FIG. 7A shows wheat FHB symptom after control of hypovirulent strains infected by p26-D4-Tri101 and p26-D4-FgPP1 measured by co-infection method (Test 1).
Figure 7B:
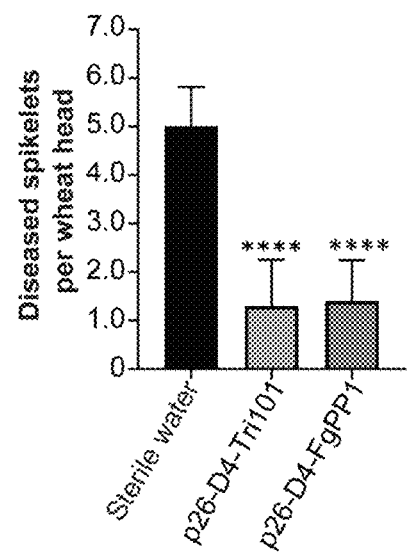
FIG. 7B shows the number of diseased spikelets per wheat head after control of hypovirulent strains infected by p26-D4-Tri101 and p26-D4-FgPP1 measured by co-infection method (Test 1).
Figure 7C:
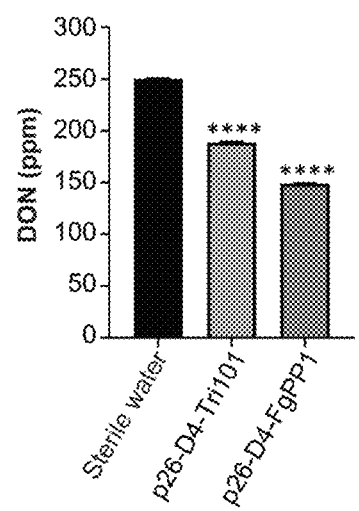
FIG. 7C shows DON concentration in infected spikelets after control of hypovirulent strains infected by p26-D4-Tri101 and p26-D4-FgPP1 measured by co-infection method (Test 1).
Figure 7E:
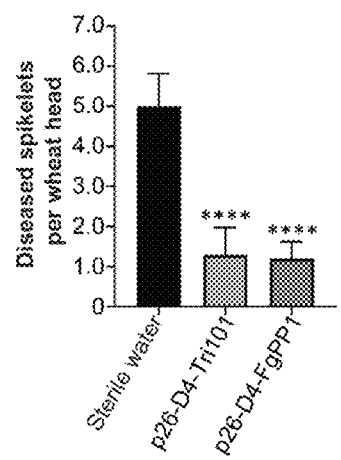
FIG. 7E shows the number of diseased spikelets per wheat head after control of hypovirulent strains infected by p26-D4-Tri101 and p26-D4-FgPP1 measured by pre-spray method (Test 2).
Figure 7F:
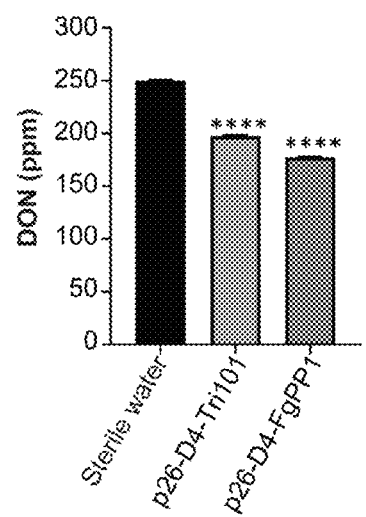
FIG. 7F shows DON concentration in infected spikelets after control of hypovirulent strains infected by p26-D4-Tri101 and p26-D4-FgPP1 measured by pre-spray method (Test 2).

FIG. 5A, FIG. 5B, and FIG. 5C show the silencing efficiency analysis of GFP gene by VIGS vector p26-D4. The results show that the GFP silencing vectors p26-D4-GFP75F, p26-D4-GFP75R, p26-D4-GFP150F, p26-D4-GFP150R, p26-D4-GFP300F, p26-D4-GFP300R, p26-D4-GFP450F and p26-D4-GFP450R constructed based on p26-D4 obtain transfectant through transfection by PEG-mediated protoplasts and re-culture (see FIG. 5B). Southern blot and sequencing analysis confirm that in the strains infected by p26-D4-GFP300F, p26-D4-GFP300R, p26-D4-GFP450F and p26-D4-GFP450R, the inserted GFP fragments of 300 bp and 450 bp are lost in the DNA-C component. However, in the strains infected by p26-D4-GFP75F, p26-D4-GFP75R, p26-D4-GFP150F and p26-D4-GFP150R, the inserted GFP fragments of 75 bp and 150 bp are capable of being stably retained in the viral DNA-C component. The strains infected by p26-D4-GFP75F, p26-D4-GFP75R, p26-D4-GFP150F and p26-D4-GFP150R show normal growth phenotype (see FIG. 5A). The fluorescence intensity is observed by fluorescence microscope, and it is found that the fluorescence intensity of GFP in the strains infected by p26-D4-GFP75F, p26-D4-GFP75R, p26-D4-GFP150F and p26-D4-GFP150R is obviously weaker than the fluorescence intensity of GFP in PH-1/GFP strain and PH-1/GFP strain infected by p26-D4 (see FIG. 5A). Quantitative polymerase chain reaction (qPCR) further proves that compared with PH-1/GFP strain and PH-1/GFP strain infected by p26-D4, the mRNA expression level of GFP in strains infected by p26-D4-GFP75F, p26-D4-GFP75R, p26-D4-GFP150F and p26-D4-GFP150R decrease by 55%-75% (as shown in FIG. 5C). Therefore, the present disclosure confirms that the VIGS silencing vector based on p26-D4 may effectively silence GFP, and the inserted fragment is about 75 bp-150 bp.

Embodiment 4 Silencing Effect of p26-D4

In this embodiment, the endogenous genes Tri101 and FgPP1 of *Fusarium graminearum* PH-1 are used as target genes to illustrate the silencing effect of p26-D4.

1. Construction of the Silencing Vectors p26-D4-Tri101 and p26-D4-FgPP1

On the basis of p26-D4 vector, VIGS vectors p26-D4-Tri101 and p26-D4-FgPP1 are constructed for target genes Tri101 and FgPP1. The specific construction method is to amplify 150 bp Tri101 and FgPP1 gene fragments by RCR method, connect the amplified fragments to p26-D4 vector by homologous recombination method, and finally obtain the target silencing vectors by screening.

The 150 bp Tri101 and FgPP1 gene fragments are amplified by specific primers, and the specific primers are shown in Table 3.

TABLE 3

Primers for construction of silencing vectors p26-D4-Tri101 and p26-D4-FgPP1

| Primer name | Primer sequence (5'-3') |
| --- | --- |
| p26-D4-Tri101-F (SEQ ID NO: 34) | CAGCACTAACACGTGTACCGGTGATTTGTACT CTGTTCCC |
| p26-D4-Tri101-R (SEQ ID NO: 35) | GTATGTCCACCCAATCATGCATGGTAGCTGGC CGAGGGTGTC |
| p26-D4-FgPP1-F (SEQ ID NO: 36) | CAGCACTAACACGTGTACCGGTACCATCTGCT TGCTCCTCGCC |
| p26-D4-FgPP1-R (SEQ ID NO: 37) | GTATGTCCACCCAATCATGCATGAAAGTCTTC CACAACTTG |

The protoplast preparation of *Fusarium graminearum* PH-1, PEG-mediated transfection of p26-D4-based gene silencing vector and observation of colony morphology of strains are all the same as those in Embodiment 1.

The sequence of the target gene Tri101 is shown in SEQ ID NO: 3:

GATTTGTACTCTGTTCCCAAGCGTCATCTTTCTCAGCGCAGCACTTCTAT

AATTTAGCGGCCTCACCTTCTGTAACACCAACACCAAGTGATTTACAAAC

ACCACCAAAATGGCTTTCAAGATACAGCTCGACACCCTCGGCCAGCTAC

C.

The target gene FgPP1 has a sequence as shown in SEQ ID NO: 4:

ACCATCTGCTTGCTCCTCGCCTACAAGATCAAGTACCCCGAAAACTTCTT

CATCCTTCGAGGTAACCACGAGTGTGCCTCCATCAACCGTATTTATGGAT

TCTACGACGAGTGCAAGCGTCGCTATAACATCAAGTTGTGGAAGACTTT

C.

2. Results

FIG. 6A, FIG. 6B, FIG. 6C, FIG. 6D, FIG. 6E, and FIG. 6F show an analysis of silencing efficiency of endogenous genes Tri101 and FgPP1 of *Fusarium graminearum*. The results show that the silencing vectors p26-D4-Tri101 and p26-D4-FgPP1 constructed based on p26-D4 obtain the transfectant by transfection of PEG-mediated protoplast and re-culture. Southern blot analysis confirms that the virus components could be effectively replicated in strains infected by p26-D4-Tri101 and p26-D4-FgPP1 (see FIG. 6A). Compared with strains infected by p26-D4, the RNA expression of the gene Tri101 in strains infected by p26-D4-Tri101 decreases by 80%, and the RNA expression of FgPP1 in strains infected by p26-D4-FgPP1 decreases by 63% (see FIG. 6B). The phenotypes of the strains infected by p26-D4-Tri101 and p26-D4-FgPP1 are not obviously abnormal, which are consistent with wild-type strain PH-1 and strains infected by p26-D4 (see FIG. 6D). In addition, the experiments of toxin production detection and pathogenicity test show that compared with strains infected by p26-D4, the DON production and pathogenicity of strains infected by p26-D4-Tri101 and p26-D4-FgPP1 are greatly reduced (see FIG. 6C, FIG. 6E and FIG. 6F). It shows that p26-D4 constructed by the disclosure is capable of effectively silencing the endogenous genes of *Fusarium graminearum*, and at the same time, it shows that the VIGS vector is capable of successfully transforming pathogenic fungal strains into hypovirulent strains.

Embodiment 5 Analysis of Biological Control Effect of VIGS-Induced Hypovirulent Strains Based on the results of Embodiment 4, the biological control effect of obtained hypovirulent strains infected by p26-D4-Tri101 and p26-D4-FgPP1 is further tested. In this embodiment, co-infection method and pre-spray method are selected to verify the biological control effect of VIGS-induced hypovirulent strains.

Co-infection method (Test 1): the mycelian blocks of the hypovirulent strains infected by p26-D4-Tri101 and p26-D4-FgPP1 are cut into small blocks with the same size and inoculated into the same spikelet together with 10 μL of PH-1 conidia suspension. After 12 days, the incidence of wheat *Fusarium* head blight (FHB) is observed, the number of diseased spikelets is counted and the content of deoxynivalenol (DON) is determined.

Pre-spray method (Test 2): the hypovirulent strains infected by p26-D4-Tri101 and p26-D4-FgPP1 are cultured in PDB liquid medium for 3 days, and the mycelium is collected, broken into small mycelium segments, and the $OD_{600} \approx 2.0$. First, the mycelium segment suspension is sprayed on wheat spikelets, and then 10 μL of PH-1 conidia suspension is inoculated after 24 h. After 12 days, the incidence of wheat FHB is observed, the number of diseased spikelets is counted and the DON content is determined.

FIG. 7A, FIG. 7B, FIG. 7C, FIG. 7D, FIG. 7E, and FIG. 7F illustrate an analysis on the control effect of VIGS-induced hypovirulent strains on wheat *Fusarium* head blight (FHB). The results show that in the co-infection method (Test 1), compared with the control group treated with sterile water, the wheat spikelets treated with hypovirulent strains infected by p26-D4-Tri101 and p26-D4-FgPP1 show obviously delayed expansion of wheat FHB spot, the protection efficiency reaches 74% and 76% respectively, and the DON content decreases by 21% and 29% respectively (see FIG. 7A, FIG. 7B, FIG. 7C). In the determination test by pre-spray method (Test 2), compared with the control group treated with sterile water, the wheat spikelets treated with hypovirulent strains infected by p26-D4-Tri101 and p26-D4-FgPP1 also show obviously delayed expansion of wheat FHB spot, the protection efficiency reaches 72% and 74% respectively, and the DON content decreases by 25% and 40% respectively (see FIG. 7D, FIG. 7E, FIG. 7F). The results show that the low-virulence strain induced by VIGS vector p26-D4 could effectively control wheat FHB under experimental conditions.

The above-mentioned embodiments only describe the preferred mode of the disclosure, and do not limit the scope of the disclosure. Under the premise of not departing from the design spirit of the disclosure, various modifications and improvements made by ordinary technicians in the field to the technical scheme of the disclosure shall fall within the protection scope determined by the claims of the disclosure.

What is claimed is:

1. A mycovirus-induced gene silencing vector, wherein its nucleotide sequence is shown in SEQ ID NO: 2.

2. A construction method for the mycovirus-induced gene silencing vector according to claim 1, comprising the following steps:
   (1) connecting three single-stranded circular DNA molecules DNA-A as shown in SEQ ID NO: 5, DNA-B as shown in SEQ ID NO: 6 and DNA-C as shown in SEQ ID NO: 7 of mycovirus FgGMTV1/HB58 in series and introducing into a same vector to construct a recombinant vector; and
   (2) carrying out a deletion mutation on a coding protein p26 of the DNA-C molecule in the recombinant vector to obtain the mycovirus-induced gene silencing vector.

3. The construction method according to claim 2, wherein 1.3 copies of the DNA-A, 1.3 copies of the DNA-B and 1.5 copies of the DNA-C are connected in series, and then connected to pBluescript II SK(+) to construct the recombinant vector.

4. The construction method according to claim 2, wherein the deletion mutation is a deletion of a sequence of 454-603nt of the coding protein p26 of the DNA-C as shown in SEQ ID NO: 7.

5. The mycovirus-induced gene silencing vector according to claim 1, wherein the mycovirus-induced gene silencing vector is contained in *Fusarium graminearum*.

6. The mycovirus-induced gene silencing vector according to claim 5, wherein the mycovirus-induced gene silencing vector carries exogenous genes, and the exogenous genes comprise Tri101 gene and FgPP1 gene.

* * * * *

SEQUENCE LISTING

```
Sequence total quantity: 37
SEQ ID NO: 1             moltype = DNA  length = 5501
FEATURE                  Location/Qualifiers
source                   1..5501
                         mol_type = other DNA
                         organism = synthetic construct
SEQUENCE: 1
aagcttgagc tcgcatgctt cggcgagttt agttgcgtcg aactcatcag gtgtttggga  60
ataagtgaaa agccattttt tacatcggag tcggtatctg tgatcactag ttagttagtt  120
gggaatagct tcactttttg gcaattgagt taagtaaggg tcattgcacc atcatggggg  180
agggacctcc gggggggccc catgtggggc tgtacccgcg tcagaagccc aagctctgga  240
ataaaaaaaa taaaaaatac gtactggttg cgttgtcgtt tttgtggctg aggtgtttct  300
gagtcacatg attcggaagc gcgtttggac attgtggctg aagagtggct ttgcggaggt  360
caagaaatct aagaaagaga ggatttaaga ttcttctctt tcttagattt gtgaccgtga  420
cccaagtttg atttatatac tagttatgtg ttgactaagg tacagagagg ggtagtgatc  480
tccacaataa tggcgttagc gtccatccat ttccaatcaa tatcagtgca ggtacggcgt  540
ggatcttcat tggctatgta gatgcacggc ttaccccaca tgacccgctg ttttcctttg  600
tacttgtcgg tagctacgaa ttctcgttgg ccgaaccatt gtttgtaatt tggaaaagag  660
gagaacccac caatcaagtc atcaaacacc gcgtagttta cgttagggtg aaagtcagag  720
agcatgaaca tgcctgggaa gtaggcgtga ttggctagac ttcgcgccca tagagtttta  780
ccgaggcggg aagcgccgaa taaaatgaga cttatgggtc ggtatgatgt gttgttcgtg  840
acgtaattgt caacccagtc tttgagttcg ggatagtcag agtaattgac agtaatttgt  900
ggagattcgt atgtgctctg tggtggaccg aatttccatt cagcaaatga cttgatgttg  960
ttccagcatt tgatggattg gttaggtagt tcggtggcag ccaagtgtaa aaattctttt  1020
gcggaagttg attggtcgat gatacgcaac cattctttat ccatgttctt ttggttcaag  1080
gatggttggt gtgggggtgt accctcttcc cattggatgt cgttatcttt ttttacgtaa  1140
ttgacgacag tgtgtggggt tctggtgaca acttcgatgt tggggtgaac accacagaaa  1200
tcgaagtccc gtgcgttgtt tgaagtgtga atagtttcaa cttcccaata cacgtgatgg  1260
tggaatccgc catctttgtg ttgttctttt gagatgacga gatagacaag aagtggactt  1320
ttttctttga acatttcggc gagtttagtt gcgtcgaact catcaggtgt ttgggaataa  1380
gtgaaaagcc atttttttaca tcggagtcgg tatctgtgat cactagttag ttagttggga  1440
atagcttcac tttttggcaa ttgagttaag taagggtcat tgcaccatca tgggggaggg  1500
acctccgggg gggccccatg tggggctgta cccgcgtcag aagcccaagc tctggaataa  1560
aaaaaataaa aaatacgtac tggttgcgtt gtcgtttttg tggctgaggt gtttctgagt  1620
cacatgattc ggaagcgcgt ttggacattg tggctgaaga gtggctttgc ggaggtcaag  1680
aaatctaaga aagagaggat ttaagattct tctctttctt agatttgtga ccgtgaccca  1740
agtttgattt atatactagg catgcgctag cggtaatttt agtgtagcaa aattgagttg  1800
gtgatagctt catttttttg gatccacttt gtgacaattg agttgaagta agggtcattg  1860
caccatcatg gggggagggac ctccgggggg gccccatgtg gggctgtacc cgcgtcagaa  1920
gcccaagctc cggaataaaa aaaaatcaaa agtagactgt cggttaaagt tcggttgggt  1980
aggattagtc agcaaatttt caaccaatag cggaggtcaa gaaatctaag aaagagagga  2040
tttaagattc ttctctttct tagatttgtg accgtgaccc aggtttgatt ttgggtatat  2100
aagggagggg tagccaccat ttttgctagt ctgtttttgg acttaaaaaa tttatttttt  2160
aacacaaaac attattacgt cgacaaaaat ggcttctaca aagaagaaat catacaacaa  2220
caagaaggct tataaaaaaa aagaatggaa gtcgaagaag acttgggaca agtctagtta  2280
ttacgacaat taccagtcga agatgaatat ttcgaatatg cagacgaaga gggacaacat  2340
gatgtgtgtg acgtcacatt gtggtgttcc gaatgcggcg ttactggaga attctgttgt  2400
gggtgaaatt ccagccaata tgggagttca ttatattatg tggtctccta cgtatcgaga  2460
ggcggtacca ccgaatcgag cggcacagtt ggatcggcaa tccgcaaaca catttttttac  2520
tggttggaag gataatttgt cctatcaatt taagggacag attacaggga ttcacctgag  2580
ggttgtgata tctacccgaa gagaagtgga gtccgcgcag ccttttattg ggccggggaa  2640
tacgctgtgc agaaacttgg cggttcgtga tatgtcggat gagacattgg accagttttt  2700
gtcgggtacc ccgggatgttg attggacgtt ggtgaatgtg atggacacga tgtttgatcc  2760
ggcggtgtgc aaggtgttgt ttcggcagag gaagatttta ggtgcagctg atgcgttgtt  2820
gaagacggag gagttttatc accgtatccg tcggcctatg gtgtacggcg ataggcagga  2880
tggtttggag tttgtgtcta gtggttgggc tggaagggag tcggagaaca tatacgtcat  2940
tgatatgtac tctttgattt cggcagcccc accgttaggt aatttgttgg atggagaggg  3000
aaatattgtt ttggatgaca agaaacggcc tattcccgta tatgcgaagt taaatattag  3060
tggaaatagt atagtgtatt ggagggagta gggtaatttt agtgtagcaa aattgagttg  3120
gtgatagctt catttttttg gatccacttt gtgacaattg agttgaagta agggtcattg  3180
caccatcatg gggggagggac ctccgggggg gccccatgtg gggctgtacc cgcgtcagaa  3240
gcccaagctc cggaataaaa aaaaatcaaa agtagactgt cggttaaagt tcggttgggt  3300
aggattagtc agcaaatttt caaccaatag cggaggtcaa gaaatctaag aaagagagga  3360
tttaagattc ttctctttct tagatttgtg accgtgaccc aggtttgatt ttgggtatat  3420
aagggagggg tagccaccat ttttgctagt ctgtttttgg acttaaaaaa tttatttttt  3480
aacacaaaac attattacgt cgacaaaagc tagcacgcgt ccatggcaat tgctttatat  3540
tgtaaaaaat atttgtaact gtaaataatt agttggtgat agcttcattt tttttactcc  3600
actttgtgac aattgagtta agtaagggtc attgcaccat catgggggag ggacctccgg  3660
gggggcccca tgtggggctg tacccgcgtc agaagcccaa gctctttgtt gagccgagcg  3720
cagcggtaat ttggagtcac gtgaggtaaa ataaaatgtg gacttacgtt cttggaattg  3780
```

```
atgattgaga cattttgaaa aagtgttgga gtggttgggg tatttatggt caaggacatg  3840
tttggtggtg tcattggtta atataggtac tgtcggtaga tagttgttgc ggttgaagta  3900
taatgcgtgg agcaccgagg tcagaacttt taggaaagac gatttaagat tctctttcct  3960
aaaagtctga ccgtgactcc ctttggcctt gacgacgtta ttggtggagg attggaatgt  4020
tacccgcaat ttcacgtgac atgtggaaat gtggtgacat gaagaattgt gggacggcac  4080
aattttaatt gggtggaaca cagcagggta ggattaggca gaatgaggca gatttaggca  4140
gcggaaattt attttaaat tggagcattg tctaaatcta gaagtacatg gtaccagtca  4200
tcatcgtttg gttgatgatc tggtatgtcc acccaatcag gatcatttaa attatgtaca  4260
attgaattgt tatgatttgt aaaaaaaaaa gataggtaat cgcataacgt gtttttgttg  4320
aataaaataa tacacgtgtt tgcgtattgt tgtaccatgt catgtgggtc gggattgttg  4380
tggagatgac acgtgttagt gctggtatga actcgcagga gtgtagtacc agtcgacaaa  4440
ggcttggatg tgttggcggt gtcgttggag tagtgtaggg tgagtttcct cgaaacgact  4500
aagaaacgcc ccttgatttg gctcggagaa aagttgttgc cagaaggggt cagatgtggc  4560
tgagcaaaga tctgcatccc cgaactgagc cacaagcacc tctttagact ggatgctctc  4620
gtataccggg cctgcatgtg tgtatattgg cagaatagaa ggcataactc cgctgtaagc  4680
gagttgtagg cttcgttgga ggggaatgtt tccagtatcg atgtagatat cgagatcaca  4740
gttcccatta gttcttgtat tgtaaccggc gatgaatctc tttggattga tgtccatttg  4800
gagttgagaa gtgaaattat ctgattgttt tgggtcgaca tcttatatt gtaaaaaata  4860
tttgtaactg taaataatta gttggtgata gcttcatttt ttttactcca ctttgtgaca  4920
attgagttaa gtaagggtca ttgcaccatc atgggggagg gacctccggg ggggcccat   4980
gtggggctgt accccgcgtca gaagccaag ctctttgttg agccgagcgc agcggtaatt   5040
tggagtcacg tgaggtaaaa taaaatgtgcg acttacgttc ttggaattga tgattgagac  5100
atttgaaaa agtgttggag tggttggggt atttatggtc aaggacatgt ttggtggtgt  5160
cattggttaa tataggtact gtcggtagat agttgttgcg gttgaagtat aatgcgtgga  5220
gcaccgaggt cagaactttt aggaaagacg atttaagatt ctctttccta aaagtctgac  5280
cgtgactccc tttggccttg acgacgttat tggtggaagg attgaatgtt acccgcaatt  5340
tcacgtgaca tgtggaaatg tggtgacatg aagaattgtg ggacggcaca attttaattg  5400
ggtggaacac agcagggtag gattaggcag aatgaggcag atttaggcag cggaaattta  5460
tttacgcgtc catggcaatt ggagctcctg caggcggccg c                     5501

SEQ ID NO: 2           moltype = DNA   length = 5369
FEATURE                Location/Qualifiers
source                 1..5369
                       mol_type = other DNA
                       organism = synthetic construct
SEQUENCE: 2
aagcttgagc tcgcatgctt cggcgagttt agttgcgtcg aactcatcag gtgtttggga    60
ataagtgaaa agccattttt tacatcggag tcggtatctg tgatcactag ttagttagtt   120
gggaatagct tcacttttg gcaattgagt taagtaaggg tcattgcacc atcatggggg   180
agggacctcc ggggggcccc catgtggggc tgtacccgcg tcagaagccc aagctctgga   240
ataaaaaaa taaaaatac gtactggttg cgttgtcgtt tttgtggctg aggtgtttct    300
gagtcacatg attcggaagc gcgtttggac attgtgctg aagagtggct ttgcggaggt   360
caaaatct aagaaagaga ggatttaaga ttcttctctt tcttagattt gtgaccgtga    420
cccaagtttg atttatatac tagttatgtg ttgactaagg tacagagagg ggtagtgatc   480
tccacaataa tggcgttagc gtccatccat ttccaatcaa tatcagtgca ggtacggcgt   540
ggatcttcat tggctatgta gatgcacggc ttaccccaca tgacccgctg tttcctttg    600
tacttgtcgg tagctacgaa ttctcgttgg ccgaaccatt gtttgtaatt tggaaaagag   660
gagaacccac caatcaagtc atcaaacacc gcgtagttta cgttagggtg aaagtcagag   720
agcatgaaca tgcctgggaa gtaggcgtga ttggctagac ttcgcgccca tagagtttta   780
ccgaggcggg aagcgccgaa taaatgaga cttatgggtc ggtatgatgt gttgttcgtg    840
acgtaattgt caacccagtc tttgagttcg ggatagtcag agtaattgac agtaaatttgt   900
ggagattcgt atgtgctctg tggtggaccg aattctccatt cagcaaatga cttgatgttg   960
ttccagcatt tgatggattg gttaggtagt tcggtggcag ccaagtgtaa aaattctttt  1020
gcggaagttg attggtcgat gatacgcaac cattctttat ccatgttctt ttggttcaag  1080
gatggttggt gtgggggtgt accctcttcc cattggattg cgttatcttt ttttacgtaa  1140
ttgacgacag tgtgtggggt tctggtgaca cttcgatgt tgggggtgaac accacagaaa  1200
tcgaagtccc gtgcgttgtt tgaagtgtga atagtttcaa cttcccaata cacgtgatgg  1260
tggaatccgc catctttgtg ttgttctttt gagatgacga gatagacaag aagtggactt  1320
ttttctttga acatttcggc gagttagtt gcgtcgaact catcaggtgt ttgggaataa  1380
gtgaaagcc attttttaca tcggagtcgg tatctgtgat cactagttag ttagttggga  1440
atagcttcac ttttggcaa ttgagttaag taagggtcat tgcaccatca tgggggaggg  1500
acctccgggg gggcccatg tggggctgta cccgcgtcag aagcccaagc tctgaataa   1560
aaaaaataaa aatacgtac tggttgcgtt gtcgtttttg gctgaggt gtttctgagt    1620
cacatgattc ggaagcgcgt ttggacattg tgctgaagag tggctttgcg gaggtcaaa   1680
aatctaaga aagaggat taagattct tctctttctt agatttgtga ccgtgaccca    1740
agtttgattt atatactagg catgcgctag cggtaatttt agtgtagcaa aattgagttg  1800
gtgatagctt cattttttg gatccacttt gtgacaattg agttgaagta agggtcattg  1860
caccatcatg ggggagggac ctccgggggg gcccatgtgg ggctgtacc cgctgtagcaa  1920
gcccaagctc cggaataaaa aaaaatcaaa agtagactgt cggttcaatt tcggttgggt  1980
aggattagtc agcaaatttt caaccaatag cggaggtcaa gaaatctaag aaagagagga  2040
tttaagattc ttctctttct tagatttgtg accgtgaccc aagtttgatt tgggtatat   2100
aagggagggg tagccaccat ttttgctagt ctgttttgg acttaaaaaa tttatttttt   2160
aacacaaaac attattacgt cgacaaaaat ggcttctaca aagaagaaat catacaacaa  2220
caagaaggct tataaaaaaa aagaatgaa gtcgaagaag acttgggaca agtctagtta  2280
ttacgacaat taccagtcga agatgaatat ttcgaatatg cagacgaaga gggacaacat  2340
gatgtgtgtg acgtcacatt gtggtgttcc gaatgcggcg ttactggaga attcgttgt   2400
gggtgaaatt ccagccaata tgggagttca ttatattatg tggtctccta cgtatcgaga  2460
ggcggtacca ccgaatcgag cggcacagtt ggatcggcaa tccgcaaaca catttttttac  2520
tggttggaag gataatttgt cctatcaatt taagggacag attacaggga ttcacctgag   2580
```

```
ggttgtgata tctacccgaa gagaagtgga gtccgcgcag cctttttattg ggccggggaa    2640
tacgctgtgc agaaacttgg cggttcgtga tatgtcggat gagacattgg accagttttt    2700
gtcgggtacc cgggatgttg attggacgtt ggtgaatgtg atggacacga tgtttgatcc    2760
ggcggtgtgc aaggtgttgt ttcggcagag aagatttta ggtgcagctg atgcgttgtt    2820
gaagacggag gagtttttatc accgtatccg tcggcctatg gtgtacggcg ataggcagga    2880
tggtttggag tttgtgtcta gtggttgggc tggaagggaa tcggagaaca tatacgtcat    2940
tgatatgtac tcttttgattt cggcagcccc accgttaggt aatttgttgg atggagaggg    3000
aaatattgtt ttggatgaca agaaacggcc tattcccgta tatgcgaagt taaatattag    3060
tggaaatagt atagtgtatt ggagggagta gggtaatttt agtgtagcaa aattgagttg    3120
gtgatagctt cattttttttg gatccacttt gtgacaattg agttgaagta agggtcattg    3180
caccatcatg ggggagggac ctccgggggg gccccatgtg gggctgtacc cgcgtcagaa    3240
gcccaagctc cggaataaaa aaaaatcaaa agtagactgt cggttaaagt tcggttgggt    3300
aggattagtc agcaaatttt caaccaatag cggaggtcaa gaaatctaag aaagagagga    3360
tttaagattc ttctctttct tagatttgtg accgtgaccc aggtttgatt ttgggtatat    3420
aagggagggg tagccaccat ttttgctagt ctgttttttgg acttaaaaaa tttatttttt    3480
aacacaaaac attattacgt cgacaaaagc tagcacgcgt ccatggcaat tgctttatat    3540
tgtaaaaaat atttgtaact gtaaataatt agttggtgat agcttcattt ttttttactcc    3600
actttgtgac aattgagtta agtaagggtc attgcaccat catgggggag ggacctccgg    3660
gggggcccca tgtggggctg tacccgcgtc agaagcccaa gctctttgtt gagccgagcg    3720
cagcggtaat ttggagtcac gtgaggtaaa ataaaatgtg gacttacgtt cttggaattg    3780
atgattgaga cattttgaaa aagtgttgga gtggttgggg tatttatggt caaggacatg    3840
tttggtggtg tcattggtta atataggtac tgtcggtaga tagttgttgc ggttgaagta    3900
taatgcgtgg agcaccgagg tcagaacttt taggaaagac gatttaagat tctctttcct    3960
aaaagtctga ccgtgactcc ctttggcctt gacgacgtta ttggtggagg attggaatgt    4020
tacccgcaat ttcacgtgac atgtgaaat gtggtgacat gaagaattgt gggacggcac    4080
aattttaatt gggtaggaaca cagcagggta ggattaggca gattaggca                4140
gcggaaattt atttttaaat tggagcattg tctaaatcta gaagtacatg gtaccagtca    4200
tcatcgtttg gttgatgatc tggtatgtcc acccaatcat gcatcctagg accggtacac    4260
gtgttagtgc tggtatgaac tcgcaggagt gtagtaccag tcgacaaagg cttggatgtg    4320
ttggcggtgt cgttggagta gtgtagggtg agtttcctcg aaacgactaa gaaacgcccc    4380
ttgattggc tcggagaaaa gttgttgcca gaagggggtca gatgtggctg agcaaagatc    4440
tgcatcccg aactgagcca caagcacctc tttagactgg atgctctcgt ataccgggcc    4500
tgcatgtgtg tatattggca gaatagaagg cataactccg ctgtaagcga gttgtaggct    4560
tcgttggagg ggaatgtttc cagtatcgat gtagatatcg agatcacagt tcccattagt    4620
tcttgtattg taaccggcga tgaatctctt tggattgatg tccatttgga gttgagaagt    4680
gaaattatct gattgtttttg ggtcgacatc tttatattgt aaaaaatatt tgtaactgta    4740
aataattagt tggtgatagc ttcattttttt ttactccact tgtgacaat tgagttaagt    4800
aagggtcatt gcaccatcat gggggaggga cctccggggg gccccatgt ggggctgtac    4860
ccgcgtcaga agcccaagct cttttgttgag ccgagcgcg cggtaatttg gagtcacgtg    4920
aggtaaaata aaatgtggac ttacgttctt ggaattgatg attgagacat tttgaaaaag    4980
tgttggagtg gttggggtat ttatggtcaa ggacatgttt ggtggtgtca ttggttaata    5040
taggtactgt cggtagatag ttgttgcggt tgaagtataa tgcgtggagc accgaggtca    5100
gaactttttag gaaagacgat ttaagattct cttttcctaaa agtctgaccg tgactccctt    5160
tggccttgac gacgttattg gtggaggatt ggaatgttac ccgcaatttc acgtgacatg    5220
tggaaatgtg gtgacatgaa gaattgtggg acggcacaat tttaattggg tggaacacag    5280
cagggtagga ttaggcagaa tgaggcagat ttaggcagcg gaaatttatt tacgcgtcca    5340
tggcaattgg agctcctgca ggcggccgc                                       5369

SEQ ID NO: 3          moltype = DNA   length = 150
FEATURE               Location/Qualifiers
source                1..150
                      mol_type = other DNA
                      organism = synthetic construct
SEQUENCE: 3
gatttgtact ctgttcccaa gcgtcatctt tctcagcgca gcacttctat aatttagcgg     60
cctcaccttc tgtaacacca acaccaagtg atttacaaac accaccaaaa tggctttcaa    120
gatacagctc gacaccctcg gccagctacc                                      150

SEQ ID NO: 4          moltype = DNA   length = 150
FEATURE               Location/Qualifiers
source                1..150
                      mol_type = other DNA
                      organism = synthetic construct
SEQUENCE: 4
accatctgct tgctcctcgc ctacaagatc aagtaccccg aaaacttctt catccttcga     60
ggtaaccacg agtgtgcctc catcaaccgt atttatggat tctacgacga gtgcaagcgt    120
cgctataaca tcaagttgtg gaagactttc                                      150

SEQ ID NO: 5          moltype = DNA   length = 1741
FEATURE               Location/Qualifiers
source                1..1741
                      mol_type = other DNA
                      organism = synthetic construct
SEQUENCE: 5
ttcggcgagt ttagttgcgt cgaactcatc aggtgtttgg gaataagtga aaagccattt     60
tttacatcgg agtcggtatc tgtgatcact agttagttag ttgggaatag cttcacttttt   120
tggcaattga gttaagtaag gtcattgca ccatcatggg ggaggacct ccggggggc       180
cccatgtggg gctgtacccg cgtcagaagc caagctctg aataaaaaaa ataaaaaat      240
acgtactggt tgcgttgtcg ttttttgtgg ctgaggtgttt ctgagtcaca tgattcgaa    300
```

```
gcgcgtttgg acattgtggc tgaagagtgg ctttgcggag gtcaagaaat ctaagaaaga  360
gaggatttaa gattcttctc tttcttagat ttgtgaccgt gacccaagtt tgatttatat  420
actagttatg tgttgactaa ggtacagaga ggggtagtga tctccacaat aatggcgtta  480
gcgtccatcc atttccaatc aatatcagtg caggtacggc gtggatcttc attggctatg  540
tagatgcacg gcttaccccca catgacccgc tgtttttcctt tgtacttgtc ggtagctacg  600
aattctcgtt ggccgaacca ttgtttgtaa tttggaaaag aggagaaccc accaatcaag  660
tcatcaaaca ccgcgtagtt tacgttaggg tgaaagtcag agagcatgaa catgcctggg  720
aagtaggcgt gattggctag acttcgcgcc catagagttt taccgaggcg ggaagcgccg  780
aataaaatga gacttatggg tcggtatgat gtgttgttcg tgacgtaatt gtcaacccag  840
tcttttgagtt cgggatagtc agagtaattg acagtaattt gtggagattc gtatgtgctc  900
tgtggtggac cgaatttcca ttcagcaaat gacttgatgt tgttccagca tttgatggat  960
tggttaggta gttcggtggc agccaagtgt aaaaattctt ttgcggaagt tgattggtcg 1020
atgatacgca accattcttt atccatgttc ttttggttca aggatggttg gtgtgggggt 1080
gtaccctctt cccattggat gtcgttatct tttttacgt aattgacgac agtgtgtggg 1140
gttctggtga caacttcgat gttggggtga acaccacaga aatcgaagtc ccgtgcgttg 1200
tttgaagtgt gaatagtttc aacttcccaa tacacgtgat ggtggaatcc gccatctttg 1260
tgttgttctt ttgagatgac gagatagaca agaagtggac ttttttctt gaacatttcg 1320
gcgagtttag ttgcgtcgaa ctcatcaggt gtttgggaat aagtgaaaag ccatttttta 1380
catcggagtc ggtatctgtg atcactagtt agttagttgg gaatagcttc actttttggc 1440
aattgagtta agtaagggtc attgcaccat catgggggag ggacctccgg gggggcccca 1500
tgtggggctg tacccgcgtc agaagcccaa gctctgaat aaaaaaaata aaaaatacgt 1560
actggttgcg ttgtcgtttt tgtggctgag tgtgtttctga gtcacatgat tcggaagcgc 1620
gtttggacat tgtggctgaa gagtggcttt gcggaggtca agaaatctaa gaaagagagg 1680
atttaagatt cttctctttc ttagatttgt gaccgtgacc caagtttgat ttatatacta 1740
g                                                                 1741

SEQ ID NO: 6          moltype = DNA   length = 1737
FEATURE               Location/Qualifiers
source                1..1737
                      mol_type = other DNA
                      organism = synthetic construct
SEQUENCE: 6
ggtaatttta gtgtagcaaa attgagttgg tgatagcttc attttttggg atccactttg   60
tgacaattga gttgaagtaa gggtcattgc accatcatgg gggagggacc tccgggggggg  120
ccccatgtgg ggctgtaccc gcgtcagaag cccaagctcc ggaataaaaa aaaatcaaaa  180
gtagactgtc ggttaaagtt cggttgggta ggattagtca gcaaattttc aaccaatagc  240
ggaggtcaag aaatctaaga agagaggat ttaagattct tctctttctt agatttgtga  300
ccgtgaccca ggtttgattt tgggtatata agggaggggg agccaccatt tttgctagtc  360
tgttttttgga cttaaaaaat ttattttta acacaaaaca ttattacgtc gacaaaaatg  420
gcttctacaa agaagaaatc atacaacaac aagaaggctt ataaaaaaa agaatggaag  480
tcgaagaaga cttgggacaa gtctagttat tacgacaatt accagtcgaa gatgaatatt  540
tcgaatatgc agacgaagag ggacaacatg atgtgtgtga cgtcacattg tggtgttccg  600
aatgccgcgt tactgggaaa ttctgtttgtg ggtgaaattc cagcaaatat ggagagttca  660
tatattatgt ggtctcctac gatcgagagg gcgtaccac gaatcgagc ggcacagttg  720
gatcggcaat ccgcaaacac atttttttact ggttggaagg ataatttgtc ctatcaattt  780
aagggacaga ttacagggat tcacctgagg gttgtgtatat ctacccgaag agaagtggag  840
tccgcgcagc ctttttattg gccggggaat acgctgtgca gaaacttggc ggttcgtgat  900
atgtcgatgc agacattgga ccagttttgt tcgggtaccc gggatgttga ttggacgttg  960
gtgaatgtga tggacacgat gttttgatccg gcgtgtgca aggtgttgtt tcggcagagg 1020
aagattttag gtgcagctga tgcgttgttg aagacggagg agttttatca ccgtatccgt 1080
cggcctatgg tgtacggcga taggcaggat ggtttgaagt ttgtgtctag tggttgggct 1140
ggaagggagt cggagaacat atacgtcatt gatatgtact ctttgatttc ggcagcccca 1200
ccgttaggta atttgttgga tggagaggga aatattgttt tggatgacaa gaaacggcct 1260
attcccgtat atgcgaagtt aaatattagt ggaaatagta tagtgtattg gagggagtag 1320
ggtaatttta gtgtagcaaa attgagttgg tgatagcttc atttttttgg atccactttg 1380
tgacaattga gttgaagtaa gggtcattgc accatcatgg gggagggacc tccgggggggg  1440
ccccatgtgg ggctgtaccc gcgtcagaag cccaagctcc ggaataaaaa aaaatcaaaa 1500
gtagactgtc ggttaaagtt cggttgggta ggattagtca gcaaattttc aaccaatagc 1560
ggaggtcaag aaatctaaga agagaggat ttaagattct tctctttctt agatttgtga 1620
ccgtgaccca ggtttgattt tgggtatata agggaggggg agccaccatt tttgctagtc 1680
tgttttttgga cttaaaaaat ttattttta acacaaaaca ttattacgtc gacaaaa   1737

SEQ ID NO: 7          moltype = DNA   length = 1931
FEATURE               Location/Qualifiers
source                1..1931
                      mol_type = other DNA
                      organism = synthetic construct
SEQUENCE: 7
ctttatattg taaaaaatat ttgtaactgt aaataattag ttggtgatag cttcattttt   60
tttactccac tttgtgacaa ttgagttaag taagggtcat tgcaccatca tgggggaggg  120
acctccgggg gggcccccatg tggggctgta cccgcgtcag aagcccaagc tctttgttga  180
gccgagcgca gcgtaatttt ggagtcacgt gaggtaaaat aaaatgtgga cttacgttct  240
tggaattgat gattgagaca tttgaaaaaa gtgttggagt ggttgggta tttatggtca  300
aggacatgtt tggtggtgtc attggttaat ataggtactg tcggtagata gttgttgcgg  360
ttgaagtata atgcgtggag caccgaggtc agaactttta ggaaagacga tttaagattc  420
tctttcctaa aagtctgacc gtgactccct ttggccttga cgacgttatt ggtgaggat  480
tggaatgtta cccgcaattt cacgtgacat gtggaaatgt ggtgacatga gaattgtgg  540
gacggcacaa ttttaattgg gtgaacaca gcagggtagg attaggcaga atgaggcaga  600
tttaggcagc ggaaatttat ttttaaattg gagcattgtc taaatctaga agtacatggt  660
```

```
accagtcatc atcgtttggt tgatgatctg gtatgtccac ccaatcagga tcatttaaat    720
tatgtacaat tgaattgtta tgatttgtaa aaaaaaaaga taggtaatcg cataacgtgt    780
ttttgttgaa taaaataata cacgtgtttt cgtattgttg taccatgtca tgtgggtcgg    840
gattgttgtg gagatgacac gtgttagtgc tggtatgaac tcgcaggagt gtagtaccag    900
tcgacaaagg cttggatgtg ttggcggtgt cgttggagta gtgtagggtg agtttcctcg    960
aaacgactaa gaaacgcccc ttgatttggc tcggagaaaa gttgttgcca gaaggggtca   1020
gatgtggctg agcaaagatc tgcatccccg aactgagcca caagcacctc tttagactgg   1080
atgctctcgt ataccgggcc tgcatgtgtg tatattggca gaatagaagg cataactccg   1140
ctgtaagcga gttgtaggct tcgttggagg ggaatgtttc cagtatcgat gtagatatcg   1200
agatcacagt tccattagt tcttgtattg taaccggcga tgaatctctt tggattgatg    1260
tccatttgga gttgagaagt gaaattatct gattgttttg ggtcgacatc tttatattgt   1320
aaaaaatatt tgtaactgta aataattagt tggtgatagc ttcatttttt ttactccact   1380
ttgtgacaat tgagttaagt aagggtcatt gcaccatcat gggggaggga cctccggggg   1440
ggcccccatgt ggggctgtac ccgcgtcaga agcccagct ctttgttgag ccgagcgcag   1500
cggtaatttg gagtcacgtg aggtaaaata aaatgtggac ttacgttctt ggaattgatg   1560
attgagacat tttgaaaaag tgttggagtg gttggggtat ttatggtcaa ggacatgttt   1620
ggtggtgtca ttggttaata taggtactgt cggtagatag ttgttgcggt tgaagtataa   1680
tgcgtggagc accgaggtca gaacttttag gaaagacgat ttaagattct ctttcctaaa   1740
agtctgaccg tgactccctt tggccttgac gacgttattg gtggaggatt ggaatgttac   1800
ccgcaatttc acgtgacatg tggaaatgtg gtgacatgaa gaattgtggg acggcacaat   1860
tttaattggg tggaacacag cagggtagga ttagcagaa tgaggcagat ttaggcagcg   1920
gaaatttatt t                                                       1931

SEQ ID NO: 8           moltype = DNA   length = 39
FEATURE                Location/Qualifiers
source                 1..39
                       mol_type = other DNA
                       organism = synthetic construct
SEQUENCE: 8
aggatgcatt acaactcgct tacagcggag ttatgcctt                           39

SEQ ID NO: 9           moltype = DNA   length = 39
FEATURE                Location/Qualifiers
source                 1..39
                       mol_type = other DNA
                       organism = synthetic construct
SEQUENCE: 9
aggaccggtc atctttatat tgtaaaaaat atttgtaac                           39

SEQ ID NO: 10          moltype = DNA   length = 39
FEATURE                Location/Qualifiers
source                 1..39
                       mol_type = other DNA
                       organism = synthetic construct
SEQUENCE: 10
aggatgcata acaactttc tccgagccaa atcaagggg                            39

SEQ ID NO: 11          moltype = DNA   length = 39
FEATURE                Location/Qualifiers
source                 1..39
                       mol_type = other DNA
                       organism = synthetic construct
SEQUENCE: 11
aggaccggtg gcttcgttgg aggggaatgt ttccagtat                           39

SEQ ID NO: 12          moltype = DNA   length = 39
FEATURE                Location/Qualifiers
source                 1..39
                       mol_type = other DNA
                       organism = synthetic construct
SEQUENCE: 12
aggatgcatc atctccacaa caatcccgac ccacatgac                           39

SEQ ID NO: 13          moltype = DNA   length = 39
FEATURE                Location/Qualifiers
source                 1..39
                       mol_type = other DNA
                       organism = synthetic construct
SEQUENCE: 13
aggaccggtg ccagaagggg tcagatgtgg ctgagcaaa                           39

SEQ ID NO: 14          moltype = DNA   length = 39
FEATURE                Location/Qualifiers
source                 1..39
                       mol_type = other DNA
                       organism = synthetic construct
SEQUENCE: 14
aggatgcatg attgggtgga cataccagat catcaacca                           39
```

-continued

```
SEQ ID NO: 15            moltype = DNA   length = 39
FEATURE                  Location/Qualifiers
source                   1..39
                         mol_type = other DNA
                         organism = synthetic construct
SEQUENCE: 15
aggaccggta cacgtgttag tgctggtatg aactcgcag                              39

SEQ ID NO: 16            moltype = DNA   length = 39
FEATURE                  Location/Qualifiers
source                   1..39
                         mol_type = other DNA
                         organism = synthetic construct
SEQUENCE: 16
aggatgcatt aaaaataaat ttccgctgcc taaatctgc                              39

SEQ ID NO: 17            moltype = DNA   length = 39
FEATURE                  Location/Qualifiers
source                   1..39
                         mol_type = other DNA
                         organism = synthetic construct
SEQUENCE: 17
aggaccggta ggatcattta aattatgtac aattgaatt                              39

SEQ ID NO: 18            moltype = DNA   length = 24
FEATURE                  Location/Qualifiers
source                   1..24
                         mol_type = other DNA
                         organism = synthetic construct
SEQUENCE: 18
cccaccggtc agcacgactt cttc                                              24

SEQ ID NO: 19            moltype = DNA   length = 25
FEATURE                  Location/Qualifiers
source                   1..25
                         mol_type = other DNA
                         organism = synthetic construct
SEQUENCE: 19
ccaatgcatg ccgtcgtcct tgaag                                             25

SEQ ID NO: 20            moltype = DNA   length = 25
FEATURE                  Location/Qualifiers
source                   1..25
                         mol_type = other DNA
                         organism = synthetic construct
SEQUENCE: 20
cccaccggtg ccgtcgtcct tgaag                                             25

SEQ ID NO: 21            moltype = DNA   length = 24
FEATURE                  Location/Qualifiers
source                   1..24
                         mol_type = other DNA
                         organism = synthetic construct
SEQUENCE: 21
ccaatgcatc agcacgactt cttc                                              24

SEQ ID NO: 22            moltype = DNA   length = 27
FEATURE                  Location/Qualifiers
source                   1..27
                         mol_type = other DNA
                         organism = synthetic construct
SEQUENCE: 22
cccaccggta tggtgagcaa gggcgag                                           27

SEQ ID NO: 23            moltype = DNA   length = 25
FEATURE                  Location/Qualifiers
source                   1..25
                         mol_type = other DNA
                         organism = synthetic construct
SEQUENCE: 23
ccaatgcatg gtgcagatga acttc                                             25

SEQ ID NO: 24            moltype = DNA   length = 25
FEATURE                  Location/Qualifiers
source                   1..25
                         mol_type = other DNA
                         organism = synthetic construct
SEQUENCE: 24
cccaccggtg gtgcagatga acttc                                             25
```

```
SEQ ID NO: 25          moltype = DNA  length = 27
FEATURE                Location/Qualifiers
source                 1..27
                       mol_type = other DNA
                       organism = synthetic construct
SEQUENCE: 25
ccaatgcata tggtgagcaa gggcgag                                              27

SEQ ID NO: 26          moltype = DNA  length = 27
FEATURE                Location/Qualifiers
source                 1..27
                       mol_type = other DNA
                       organism = synthetic construct
SEQUENCE: 26
cccaccggtc agcacgactt cttcaag                                              27

SEQ ID NO: 27          moltype = DNA  length = 25
FEATURE                Location/Qualifiers
source                 1..25
                       mol_type = other DNA
                       organism = synthetic construct
SEQUENCE: 27
ccaatgcatg gcgagctgca cgctg                                                25

SEQ ID NO: 28          moltype = DNA  length = 26
FEATURE                Location/Qualifiers
source                 1..26
                       mol_type = other DNA
                       organism = synthetic construct
SEQUENCE: 28
cccaccggtg gcgagctgca cgctgc                                               26

SEQ ID NO: 29          moltype = DNA  length = 27
FEATURE                Location/Qualifiers
source                 1..27
                       mol_type = other DNA
                       organism = synthetic construct
SEQUENCE: 29
ccaatgcatc agcacgactt cttcaag                                              27

SEQ ID NO: 30          moltype = DNA  length = 27
FEATURE                Location/Qualifiers
source                 1..27
                       mol_type = other DNA
                       organism = synthetic construct
SEQUENCE: 30
cccaccggta tggtgagcaa gggcgag                                              27

SEQ ID NO: 31          moltype = DNA  length = 25
FEATURE                Location/Qualifiers
source                 1..25
                       mol_type = other DNA
                       organism = synthetic construct
SEQUENCE: 31
ccagttgtgg ctgttgtagt tgtac                                                25

SEQ ID NO: 32          moltype = DNA  length = 25
FEATURE                Location/Qualifiers
source                 1..25
                       mol_type = other DNA
                       organism = synthetic construct
SEQUENCE: 32
cccaccggtg ttgtggctgt tgtag                                                25

SEQ ID NO: 33          moltype = DNA  length = 27
FEATURE                Location/Qualifiers
source                 1..27
                       mol_type = other DNA
                       organism = synthetic construct
SEQUENCE: 33
ccaatgcata tggtgagcaa gggcgag                                              27

SEQ ID NO: 34          moltype = DNA  length = 40
FEATURE                Location/Qualifiers
source                 1..40
                       mol_type = other DNA
                       organism = synthetic construct
SEQUENCE: 34
```

```
cagcactaac acgtgtaccg gtgatttgta ctctgttccc                        40

SEQ ID NO: 35           moltype = DNA  length = 42
FEATURE                 Location/Qualifiers
source                  1..42
                        mol_type = other DNA
                        organism = synthetic construct
SEQUENCE: 35
gtatgtccac ccaatcatgc atggtagctg gccgagggtg tc                     42

SEQ ID NO: 36           moltype = DNA  length = 43
FEATURE                 Location/Qualifiers
source                  1..43
                        mol_type = other DNA
                        organism = synthetic construct
SEQUENCE: 36
cagcactaac acgtgtaccg gtaccatctg cttgctcctc gcc                    43

SEQ ID NO: 37           moltype = DNA  length = 41
FEATURE                 Location/Qualifiers
source                  1..41
                        mol_type = other DNA
                        organism = synthetic construct
SEQUENCE: 37
gtatgtccac ccaatcatgc atgaaagtct tccacaactt g                      41
```